(12) United States Patent
Yamamuro et al.

(10) Patent No.: US 8,476,305 B2
(45) Date of Patent: Jul. 2, 2013

(54) THERAPEUTIC AGENT OR PROPHYLACTIC AGENT FOR INFLAMMATORY BOWEL DISEASE COMPRISING AMINO ALCOHOL DERIVATIVE AS ACTIVE INGREDIENT

(75) Inventors: Naoya Yamamuro, Tochigi (JP); Koichi Nakamaru, Tochigi (JP); Tokutarou Yasue, Tochigi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 313 days.

(21) Appl. No.: 12/866,576

(22) PCT Filed: Feb. 6, 2009

(86) PCT No.: PCT/JP2009/052037
§ 371 (c)(1),
(2), (4) Date: Aug. 6, 2010

(87) PCT Pub. No.: WO2009/099174
PCT Pub. Date: Aug. 13, 2009

(65) Prior Publication Data
US 2010/0324057 A1 Dec. 23, 2010

(30) Foreign Application Priority Data
Feb. 7, 2008 (JP) ................. P2008-028070

(51) Int. Cl.
*C07C 215/00* (2006.01)
*A61K 31/00* (2006.01)

(52) U.S. Cl.
USPC ........... 514/357; 514/649; 514/651; 514/653; 564/355

(58) Field of Classification Search
None
See application file for complete search history.

(56) References Cited

U.S. PATENT DOCUMENTS

| | | | |
|---|---|---|---|
| 5,229,363 A | 7/1993 | Hammond et al. |
| 5,284,971 A | 2/1994 | Walker et al. |
| 5,447,922 A | 9/1995 | Lawrence et al. |
| 5,604,229 A | 2/1997 | Fujita et al. |
| 5,830,868 A | 11/1998 | Bolton et al. |
| 5,948,820 A | 9/1999 | Fujita et al. |
| 6,004,565 A | 12/1999 | Chiba et al. |
| 6,214,873 B1 | 4/2001 | Adachi et al. |
| 6,306,909 B1 | 10/2001 | Weaver et al. |
| 6,489,331 B1 | 12/2002 | Shimada et al. |
| 6,960,692 B2 | 11/2005 | Kohno et al. |
| 6,963,012 B2 | 11/2005 | Kohno et al. |
| 7,119,138 B1 | 10/2006 | Feeney et al. |
| 7,179,817 B2 | 2/2007 | Seko et al. |
| 7,288,558 B2 | 10/2007 | Nakade et al. |
| 7,456,157 B2 | 11/2008 | Kohno et al. |
| 7,482,491 B2 | 1/2009 | Kohno et al. |
| 7,759,326 B2 | 7/2010 | Kohno et al. |
| 7,763,752 B2 | 7/2010 | Kohno et al. |
| 2002/0040050 A1 | 4/2002 | Xu et al. |
| 2002/0091105 A1 | 7/2002 | Mandala et al. |
| 2002/0143034 A1 | 10/2002 | Taniguchi et al. |
| 2003/0003099 A1 | 1/2003 | Lake et al. |
| 2003/0018193 A1 | 1/2003 | Ohkubo et al. |
| 2003/0236297 A1 | 12/2003 | Nishi et al. |
| 2004/0033995 A1 | 2/2004 | Reid et al. |
| 2004/0058894 A1 | 3/2004 | Doherty et al. |
| 2004/0067908 A1 | 4/2004 | Nakade et al. |
| 2004/0087662 A1 | 5/2004 | Bigaud et al. |
| 2004/0110728 A1 | 6/2004 | Macdonald et al. |
| 2004/0138462 A1 | 7/2004 | Sakurai et al. |
| 2004/0147490 A1 | 7/2004 | Albert et al. |
| 2004/0224941 A1 | 11/2004 | Seko et al. |
| 2004/0235794 A1 | 11/2004 | Nakade et al. |
| 2004/0242654 A1 | 12/2004 | Kohno et al. |
| 2004/0248952 A1 | 12/2004 | Pan et al. |
| 2004/0254222 A1 | 12/2004 | Kohno et al. |
| 2005/0009786 A1 | 1/2005 | Pan et al. |
| 2005/0020837 A1 | 1/2005 | Doherty et al. |
| 2005/0033055 A1 | 2/2005 | Bugianesi et al. |
| 2005/0043386 A1 | 2/2005 | Nishi et al. |
| 2005/0107345 A1 | 5/2005 | Doherty et al. |
| 2005/0222422 A1 | 10/2005 | Lynch et al. |

(Continued)

FOREIGN PATENT DOCUMENTS

| | | |
|---|---|---|
| CN | 1561331 A | 1/2005 |
| EP | 0778263 | 6/1997 |

(Continued)

OTHER PUBLICATIONS

Vippagunta et al (Adv Drug Deliv Rev 48:3-26, 2001).*

(Continued)

*Primary Examiner* — Sreeni Padmanabhan
*Assistant Examiner* — Svetlana M Ivanova
(74) *Attorney, Agent, or Firm* — Wenderoth, Lind & Ponack, L.L.P.

(57) ABSTRACT

A novel therapeutic agent or prophylactic agent for an inflammatory bowel disease is provided. An amino alcohol derivative represented by the general formula (1):

[Chemical formula 1]

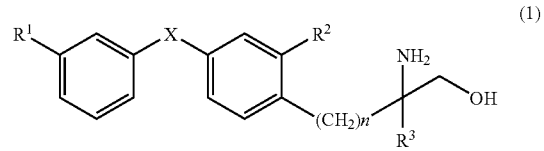

which is a sphingosine-1-phosphate receptor agonist or a pharmaceutically acceptable salt or hydrate thereof are a therapeutic agent or prophylactic agent for an inflammatory bowel disease comprises.

4 Claims, No Drawings

U.S. PATENT DOCUMENTS

| | | |
|---|---|---|
| 2005/0245575 A1 | 11/2005 | Chen et al. |
| 2006/0046979 A1 | 3/2006 | Foster et al. |
| 2006/0089334 A1 | 4/2006 | Budhu et al. |
| 2006/0135622 A1* | 6/2006 | Kohno et al. ............... 514/649 |
| 2006/0135786 A1 | 6/2006 | Saha et al. |
| 2006/0148830 A1 | 7/2006 | Terakado et al. |
| 2006/0148844 A1 | 7/2006 | Nakade et al. |
| 2006/0160771 A1 | 7/2006 | Kohno et al. |
| 2006/0161005 A1 | 7/2006 | Doherty et al. |
| 2006/0166940 A1 | 7/2006 | Buehlmayer et al. |
| 2006/0211656 A1 | 9/2006 | Albert et al. |
| 2006/0211658 A1 | 9/2006 | Hinterding et al. |
| 2006/0252741 A1 | 11/2006 | Colandrea et al. |
| 2006/0264403 A1 | 11/2006 | Albert |
| 2007/0010494 A1 | 1/2007 | Ehrhardt et al. |
| 2007/0043014 A1 | 2/2007 | Doherty et al. |
| 2007/0088002 A1 | 4/2007 | Lynch et al. |
| 2007/0088027 A1 | 4/2007 | Seko et al. |
| 2007/0135501 A1 | 6/2007 | Hinterding et al. |
| 2007/0149597 A1 | 6/2007 | Nishi et al. |
| 2007/0167410 A1 | 7/2007 | Pan et al. |
| 2007/0167425 A1 | 7/2007 | Nakade et al. |
| 2007/0191468 A1 | 8/2007 | Nishi et al. |
| 2007/0203100 A1 | 8/2007 | Pan et al. |
| 2007/0225260 A1 | 9/2007 | Hinterding et al. |
| 2008/0025973 A1 | 1/2008 | Fleenor et al. |
| 2008/0027508 A1 | 1/2008 | Chu |
| 2008/0032923 A1 | 2/2008 | Kudou et al. |
| 2008/0033024 A1 | 2/2008 | Sandanayaka et al. |
| 2008/0153882 A1 | 6/2008 | Nishi et al. |
| 2008/0161410 A1 | 7/2008 | Kusters et al. |
| 2008/0200438 A1 | 8/2008 | Albert et al. |
| 2008/0207584 A1 | 8/2008 | Habashita et al. |
| 2008/0207941 A1 | 8/2008 | Tsubuki et al. |
| 2008/0249093 A1 | 10/2008 | Colandrea et al. |
| 2009/0023797 A1 | 1/2009 | Azzaoui et al. |
| 2009/0082311 A1 | 3/2009 | Kiuchi et al. |
| 2009/0137685 A1 | 5/2009 | Kojima et al. |
| 2009/0156653 A1 | 6/2009 | Kohno et al. |
| 2009/0253802 A1 | 10/2009 | Kaneko et al. |
| 2009/0325907 A1 | 12/2009 | Kohno et al. |
| 2010/0010000 A1 | 1/2010 | Kohno et al. |
| 2010/0093745 A1 | 4/2010 | Kuriyama et al. |

FOREIGN PATENT DOCUMENTS

| | | |
|---|---|---|
| EP | 1 002 792 | 5/2000 |
| EP | 1092435 | 4/2001 |
| EP | 1 431 275 | 6/2004 |
| EP | 1 431 284 | 6/2004 |
| EP | 1602660 | 12/2005 |
| GB | 2 400 318 | 10/2004 |
| JP | 05-70495 | 3/1993 |
| JP | 07-509462 | 10/1995 |
| JP | 2579602 | 11/1996 |
| JP | 9-504547 | 5/1997 |
| JP | 11-080026 | 3/1999 |
| JP | 2000-502050 | 2/2000 |
| JP | 2000-154151 | 6/2000 |
| JP | 2001-515483 | 9/2001 |
| JP | 2002-053575 | 2/2002 |
| JP | 2002-167382 | 6/2002 |
| JP | 2002-316985 | 10/2002 |
| JP | 2002-534415 | 10/2002 |
| JP | 2003-137894 | 5/2003 |
| JP | 2003-523339 | 8/2003 |
| JP | 2003-267936 | 9/2003 |
| JP | 2004-137208 | 5/2004 |
| JP | 2004-307439 | 11/2004 |
| JP | 2004-307440 | 11/2004 |
| JP | 2004-307441 | 11/2004 |
| JP | 2004-307442 | 11/2004 |
| JP | 2005-41867 | 2/2005 |
| JP | 2005-047899 | 2/2005 |
| JP | 2007-169194 | 7/2007 |
| JP | 2008-231027 | 10/2008 |
| JP | 2008-239546 | 10/2008 |
| WO | 94/02448 | 3/1994 |
| WO | 94/08943 | 4/1994 |
| WO | 96/06068 | 2/1996 |
| WO | 97/18207 | 5/1997 |
| WO | 98/45249 | 10/1998 |
| WO | 00/01388 | 1/2000 |
| WO | 00/40560 | 7/2000 |
| WO | 01/98301 | 12/2001 |
| WO | 02/06268 | 1/2002 |
| WO | 02/08189 | 1/2002 |
| WO | 02/18395 | 3/2002 |
| WO | 02/062389 | 8/2002 |
| WO | 02/064616 | 8/2002 |
| WO | 02/067915 | 9/2002 |
| WO | 02/076995 | 10/2002 |
| WO | 02/092068 | 11/2002 |
| WO | 02/094770 | 11/2002 |
| WO | 02/100148 | 12/2002 |
| WO | 03/020313 | 3/2003 |
| WO | 03/029184 | 4/2003 |
| WO | 03/029205 | 4/2003 |
| WO | 03/040097 | 5/2003 |
| WO | 03/051876 | 6/2003 |
| WO | 03/061567 | 7/2003 |
| WO | 03/062248 | 7/2003 |
| WO | 03/062252 | 7/2003 |
| WO | 03/073986 | 9/2003 |
| WO | 03/074008 | 9/2003 |
| WO | 03/105771 | 12/2003 |
| WO | 2004/002531 | 1/2004 |
| WO | 2004/010949 | 2/2004 |
| WO | 2004/024673 | 3/2004 |
| WO | 2004/026817 | 4/2004 |
| WO | 2004/058149 | 7/2004 |
| WO | 2004/071442 | 8/2004 |
| WO | 2004/074297 | 9/2004 |
| WO | 2004/096752 | 11/2004 |
| WO | 2004/096757 | 11/2004 |
| WO | 2004/103279 | 12/2004 |
| WO | 2004/103306 | 12/2004 |
| WO | 2004/103309 | 12/2004 |
| WO | 2004/110979 | 12/2004 |
| WO | 2004/113330 | 12/2004 |
| WO | 2005/014525 | 2/2005 |
| WO | 2005/014603 | 2/2005 |
| WO | 2005/020882 | 3/2005 |
| WO | 2005/021503 | 3/2005 |
| WO | 2005/032465 | 4/2005 |
| WO | 2005/040091 | 5/2005 |
| WO | 2005/041899 | 5/2005 |
| WO | 2005/044780 | 5/2005 |
| WO | 2005/058848 | 6/2005 |
| WO | 2005/063671 | 7/2005 |
| WO | 2005/070886 | 8/2005 |
| WO | 2005/079788 | 9/2005 |
| WO | 2005/082089 | 9/2005 |
| WO | 2005/082841 | 9/2005 |
| WO | 2005/085179 | 9/2005 |
| WO | 2005/105146 | 11/2005 |
| WO | 2005/118523 | 12/2005 |
| WO | 2006/001463 | 1/2006 |
| WO | 2006/009092 | 1/2006 |
| WO | 2006/011554 | 2/2006 |
| WO | 2006/020951 | 2/2006 |
| WO | 2006/041015 | 4/2006 |
| WO | 2006/041019 | 4/2006 |
| WO | 2006/063033 | 6/2006 |
| WO | 2006/129688 | 12/2006 |
| WO | 2006/137509 | 12/2006 |
| WO | 2007/028821 | 3/2007 |
| WO | 2007/043433 | 4/2007 |
| WO | 2007/043568 | 4/2007 |
| WO | 2007/091501 | 8/2007 |
| WO | 2007/126042 | 11/2007 |
| WO | 2008/018427 | 2/2008 |
| WO | 2008/018447 | 2/2008 |
| WO | 2008/019306 | 2/2008 |
| WO | 2008/099781 | 8/2008 |

| WO | 2009/119395 | 10/2009 |
| WO | 2009/142194 | 11/2009 |
| WO | 2009/142195 | 11/2009 |

OTHER PUBLICATIONS

Han (Advances in Characterization of Pharmaceutical Hydrates. Trends in Bio/Pharmaceutical Industry, pp. 25-29. Mar. 2006).*
International Search Report issued Mar. 3, 2009 in International (PCT) Application No. PCT/JP2009/052037.
Brinkmann et al., The Immune Modulator FTY720 Targets Sphingosine 1-Phosphate Receptors, J. Biol. Chem., 2002, vol. 277, No. 24, pp. 21453-21457.
Campbell et al., The Synthesis of Novel Amino Acids via Hydroboration-Suzuki Cross Coupling, Tetrahedron Letters, 1999, vol. 40, pp. 5263-5266.
Chisari, Francis V., Cytotoxic T Cells and Viral Hepatitis, J. Clin. Invest., Apr. 1997, vol. 99, No. 7, pp. 1472-1477.
Collier et al., The direct synthesis of novel enantiomerically pure α-amino acids in protected form via Suzuki cross-coupling, Tetrahedron Letters, 2000, vol. 41, pp. 7115-7119.
Ebers, George C., Randomised double-blind placebo-controlled study of interferon β-1a in relapsing/remitting multiple sclerosis, Lancet, Nov. 7, 1998, vol. 352, pp. 1498-1501.
Forrest et al., Immune Cell Regulation and Cardiovascular Effects of Sphingosine 1-Phosphate Receptor Agonists in Rodents are Mediated via Distinct Receptor Subtypes, J. Pharm. Exp. Ther., 2004, vol. 309, No. 2, pp. 758-768.
Fried et al., Peginterferon Alfa-2a Plus Ribavirin for Chronic Hepatitis C Virus Infection, N. Engl. J. Med., Sep. 26, 2002, vol. 347, No. 13, pp. 975-982.
Ganem et al., The Molecular Biology of the Hepatitis B Virus, Annu. Rev. Biochem., 1987, vol. 56, pp. 651-693.
Gon et al., $S1P_3$ receptor-induced reorganization of epithelial tight junctions comprises lung barrier integrity and is potentiated by TNF, PNAS, Jun. 28, 2005, vol. 102, No. 26, pp. 9270-9275.
Goodin et al., Disease modifying therapies in multiple sclerosis; Report of the Therapeutics and Technology Assessment Subcommittee of the American Academy of Neurology and the MS Council for Clinical Practice Guidelines, Neurology, 2002, vol. 58, pp. 169-178.
Hashimoto et al., "β-Phenylselenoalanine as a dehydroalanine precursor-efficient synthesis of alternariolide (AM-toxin I)", Chem. Commun., 1996, pp. 1139-1140.
Hinterding et al., Synthesis of Chiral Analogues of FTY720 and its Phosphate, Synthesis, 2003, No. 11, pp. 1667-1670.
IFNB Multiple Sclerosis Study Group, Interferon beta-1b is effective in relapsing-remitting multiple sclerosis. I. Clinical results of a multicenter, randomized, double-blind, placebo-controlled trial, Neurology, Apr. 1993, vol. 43, pp. 655-661.
Igarashi, Yasuyuki, Sphingosine-1-Phosphate as an Intercellular Signaling Molecule, Ann. NY Acad. Sci., 1998, vol. 845, pp. 19-31.
Jacobs et al., Intramuscular Interferon Beta-1a for Disease Progression in Relapsing Multiple Sclerosis, Ann. Neurol., 1996, vol. 39, No. 3, pp. 285-294.
Johnson et al., Copolymer 1 reduces relapse rate and improves disability in relapsing-remitting multiple sclerosis: Results of a phase III multicenter, double-blind, placebo-controlled trial, Neurology, Jul. 1995, vol. 45, pp. 1268-1276.
Kaneko et al., Sphingosine-1-phosphate receptor agonists suppress concanavalin A-induced hepatic injury in mice, Biochem. and Biophys. Res. Commun., 2006, vol. 345, pp. 85-92.
Kappos et al., Oral Fingolimod (FTY720) for Relapsing Multiple Sclerosis, N. Engl. J. Med., Sep. 14, 2006, vol. 355, No. 11, pp. 1124-1140.
Keller et al., Immunomodulator FTY720 Induces Myofibroblast Differentiation via the Lysophospholipid Receptor $S1P_3$ and Smad3 Signaling, Am. J. Pathology, Jan. 2007, vol. 170, No. 1, pp. 281-292.
Kiuchi et al., Synthesis and Immunosuppressive Activity of 2-Substituted 2-Aminopropane-1,3-diols and 2-Aminoethanols, J. Med. Chem., 2000, vol. 43, pp. 2946-2961.
Klein et al., Total Synthesis and Antifungal Evaluation of Cyclic Aminohexapeptides, Bioorg. Med. Chem., 2000, vol. 8, pp. 1677-1696.
Levkau et al., High-Density Lipoprotein Stimulates Myocardial Perfusion in Vivo, Circulation, 2004, vol. 110, pp. 3355-3359.
Long et al., Enantioselective syntheses of homophenylalanine derivatives via nitron 1,3-dipolar cycloaddition reactions with styrenes, Tetrahedron Letters, 2001, vol. 42, pp. 5343-5345.
Mailliard et al., Suppressing Hepatitis B without Resistance—So Far, So Good, N. Engl. J. Med., Feb. 27, 2003, vol. 348, No. 9, pp. 848-850.
Mandala et al., Alteration of Lymphocyte Trafficking by Sphingosine-1-Phosphate Receptor Agonists, Science, Apr. 12, 2002, vol. 296, pp. 346-349.
Niessen et al., Dentritic cell PAR1-S1P3 signalling couples coagulation and inflammation, Nature, Apr. 3, 2008, vol. 452, No. 3, pp. 654-658.
Okazaki et al., Molecular Cloning of a Novel Putative G Protein-Coupled Receptor Expressed in the Cardiovascular System, Biochem. and Biophys. Res. Commun., 1993, vol. 190, No. 3, pp. 1104-1106.
Paty et al., Interferon beta-1b is effective in relapsing-remitting multiple sclerosis. II. MRI analysis results of a multicenter, randomized, double-blind, placebo-controlled trial, Neurology, Apr. 1993, vol. 43, pp. 662-667.
Rudick et al., Management of Multiple Sclerosis, N. Engl. J. Med., Nov. 27, 1997, vol. 337, No. 22, pp. 1604-1611.
Saito et al., Hepatitis C virus infection is associated with the development of hepatocellular carcinoma, Proc. Natl. Acad. Sci. USA, Sep. 1990, vol. 87, pp. 6547-6549.
Salomone et al., $S1P_3$ receptors mediate the potent constriction of cerebral arteries by sphingosine-1-phosphate, Eur. J. Pharmacol., 2003, vol. 469, pp. 125-134.
Sanna et al., Sphingosine 1-Phosphate (S1P) Receptor Subtypes $S1P_1$ and $S1P_3$, Respectively, Regulate Lymphocyte Recirculation and Heart Rate, J. Biol. Chem., Apr. 2, 2004, vol. 279, No. 14, pp. 13839-13848.
Shimizu et al., KRP-203, a Novel Synthetic Immunosuppressant, Prolongs Graft Survival and Attenuates Chronic Rejection in Rat Skin and Heart Allografts, Circulation, 2005, vol. 111, pp. 222-229.
Takahashi et al., A Novel Immunomodulator KRP-203 Combined with Cyclosporine Prolonged Graft Survival and Abrogated Transplant Vasculopathy in Rat Heart Allografts, Transplant. Proc., 2005, vol. 37, pp. 143-145.
Takuwa et al., Subtype-specific, differential activities of the EDG family receptors for sphingosine-1-phosphate, a novel lysophospholipid mediator, Mol. Cell. Endocrinol., 2001, vol. 177, pp. 3-11.
Viscido et al., Inflammatory bowel diseases: clinical update of practical guidelines, Nucl. Med. Commun., 2005, vol. 26, No. 7, pp. 649-655.
Weinshenker et al., A Randomized Trial of Plasma Exchange in Acute Central Nervous System Inflammatory Demyelinating Disease, Ann. Neurol., 1999, vol. 46, No. 6, pp. 878-886.
Zivadinov et al., Effects of IV methylprednisolone on brain atrophy in relapsing-remitting MS, Neurology, 2001, vol. 57, pp. 1239-1247.
Kohno, Yasushi et al., "Discovery of KRP-203, A potent and orally active new type of immunosuppressant, Sphingosine-1-phosphate receptor agonist", American Chemical Society, National meeting, Washington, D.C., vol. 229, No. Part 2, Mar. 1, 2005, pp. U150, XP008071718.
Daniel, Carolin, et al., "Therapeutic effects of the new lymphocyte homing reagent FTY720 in TNBS-colitis", Gastroenterology, vol. 128, No. 4, Suppl. 2, Apr. 2005, pp. A199, XP009128860.
Australian Office Action issued Mar. 7, 2007 in Australian Application No. 2002332289.
Canadian Office Action issued Mar. 9, 2009 in Canadian Application No. 2,461,212.
Chinese Office Action issued Apr. 22, 2005 in Chinese Patent Application No. 02819062.9 (English translation).
Chinese Office Action issued Aug. 25, 2006 in Chinese Patent Application No. 02819062.9 (English translation).
Chinese Office Action issued Nov. 4, 2005 in Chinese Patent Application No. 02819062.9 (English translation).
Indian Office Action issued Apr. 9, 2008 in Indian Application No. 687/DELNP/2004 (English translation).

Indian Office Action issued Mar. 27, 2009 in Indian Application No. 687/DELNP/2004 (English translation).
Mexican Office Action dated Apr. 18, 2007 in Mexican Patent Application No. 4002679 (English translation).
United States Office Action mailed Dec. 21, 2004 in U.S. Appl. No. 10/489,820.
Supplementary European Search Report mailed Jan. 18, 2006 in Application No. 02768057.8.
United States Office Action mailed Dec. 21, 2004 in U.S. Appl. No. 10/490,345.
Supplementary European Search Report mailed Apr. 21, 2006 in Application No. 02768056.
Australian Office Action dated Oct. 3, 2008 in Australian Application No. 2003264430.
Chinese Office Action issued Jun. 23, 2006 in Chinese Patent Application No. 03822466.6 (with English translation).
Letter Regarding Indian Office Action in Indian Patent Application No. 01427/DELNP/2005, dated Dec. 11, 2006.
Indian Office Action dated Nov. 2, 2006 in Indian Patent Application No. 01427/DELNP/2005 (English translation only).
Letter Regarding Indian Office Action in Indian Patent Application No. 01427/DELNP/2005 (English translation only), dated Oct. 25, 2007.
United States Office Action mailed Aug. 24, 2007 in U.S. Appl. No. 10/528,240.
United States Office Action mailed Feb. 13, 2008 in U.S. Appl. No. 10/528,240.
Chinese Office Action issued Oct. 27, 2006 in Chinese Patent Application No. 200480004551 (with English translation).
European Office Action dated May 19, 2008 in European Application No. 04 712 184.3.
Indian Office Action dated Apr. 2, 2009 in Indian Patent Application 3970/DELNP/2005 (English translation only).
Letter Regarding Indian Patent Application 3970/DELNP/2005 (English translation only), dated Apr. 30, 2008.
United States Office Action dated Apr. 21, 2008 in U.S. Appl. No. 10/545,790.
United States Office Action dated Oct. 29, 2007 in U.S. Appl. No. 10/545,790.
Supplementary European Search Report dated Feb. 20, 2008 in Patent Application No. 04712184.3.
Supplementary European Search Report dated Jun. 9, 2009 in Application No. 05766305.
United States Office Action dated Apr. 14, 2009 in U.S. Appl. No. 11/631,128.
United States Office Action dated Jun. 27, 2008 in U.S. Appl. No. 11/631,128.
Blam, Michael E., et al. Integrating Anti-Tumor Necrosis Factor Therapy in Inflammatory Bowel Disease: Current and Future Perspectives, The American Journal of Gastroenterology, vol. 96, No. 7 (2001).
Letter regarding Ecuadorian Application No. SP-08-8662PCT (English translation only), dated Jan. 28, 2009.
Letter Regarding Ecuadorian Application No. SP-09-9149PCT (English translation only), dated Aug. 17, 2009.
Letter Regarding Ecuadorian Application No. SP-09-9159PCT (English translation only), dated Aug. 27, 2009.
Supplementary European Search Report issued Feb. 16, 2010 in European Application No. 07713815.4-2123.
Deguchi, Yasuyuki et al., "Effects of FTY720 on DSS-induced enteritis in mice", Presented at Area 15, Kobe, International Exhibition Hall Building 1, $2^{nd}$ floor, Oct. 6, 2005, Japanese Society of Gastroenterology (abstract).
The Merck Manual, Chapter 31: Inflammatory Bowel Diseases, $17^{th}$ edition (1999), pp. 302-307.
Podolsky, Daniel K., Inflammatory Bowel Disease, N. Engl. J. Med., Aug. 8, 2002, vol. 347, No. 6, pp. 417-429.

* cited by examiner

THERAPEUTIC AGENT OR PROPHYLACTIC AGENT FOR INFLAMMATORY BOWEL DISEASE COMPRISING AMINO ALCOHOL DERIVATIVE AS ACTIVE INGREDIENT

TECHNICAL FIELD

The present invention relates to a therapeutic agent for inflammatory bowel disease, which comprises an amino alcohol derivative, a pharmacologically acceptable salt thereof or hydrate thereof as an active ingredient, or a method for treating inflammatory bowel disease.

BACKGROUND OF THE INVENTION

Inflammatory bowel disease, wherein Crohn's disease and ulcerative colitis are its main typical diseases, is an intractable disease which occurs at a relatively young generation and causes symptoms such as abdominal pain, fever, diarrhea and melena. Crohn's disease is a idiopathic granulomatous inflammatory disorder in which lesion progresses from ulcer, fibrosis and then to stricture, in discontinuously from mucosa to whole layers of intestinal tract through all digestive tracts from mouth to anus, and is defined as a disorder that shows systemic symptoms such as abdominal pain, chronic diarrhea, fever and malnutrition. Also, ulcerative colitis is an idiopathic diffuse non-specific inflammation of the large intestine, which mainly affects mucosa and frequently forms erosion and ulcer and is a disease which shows various general symptoms including bloody diarrhea. Other inflammatory bowel diseases, namely enteritis occurring in small intestine or large intestine, include intestinal Behcet's disease, hemorrhagic rectal ulcer, pouchitis and the like. Regarding the cause of inflammatory bowel disease, it is considered that an abnormal immune function is concerned, but its exact cause is not known yet (Non-patent Reference 1 and 2).

Immunosuppressants, steroids, salazosulfa-pyridine, mesalazine and the like are used in the medication of inflammatory bowel disease. Regarding the immunosuppressants, it is said that antimetabolites, particularly azathiopurine, 6-mercaptopurine and the like, are effective for Crohn's disease, but these are low in the clinical effect at early stage of administration and frequently show side effects such as allergy, pancreatitis and leukopenia. Ciclosporin at a high dose shows therapeutic effect for inflammatory and fistula diseases, but its long-term use is contraindication because of various toxicities. A monoclonal antibody or infliximab which inhibits tumor necrosis factor is used by intravenous injection for moderate or severe Crohn's disease (particularly accompanied by fistulas) having resistance to other treatments, but its long-term effects and side effects have not been revealed. As the other convincing immune regulation therapy, an interleukin-1 inhibitor, an antibody for interleukin-12, an anti-CD4 antibody, an adherent molecule inhibitor, a down regulatory cytokine or a monoclonal antibody for tumor necrosis factor have been tried. Though there are many such experiential therapeutic approaches, the current drug therapy for inflammatory bowel disease is imperfect. Accordingly, it has been hoped the development of a medicine which is further effective with high safety (Non-patent References 3, 4 and 5).

Non-patent Reference 1: Research and Study Group on Specific Disease Intractable Inflammatory Intestinal Disease, Ministry of Welfare, Research Report in 1997

Non-patent Reference 2: New Engl. J. Med., 2002, 347: 417-429

Non-patent Reference 3: Am. J. Gastroenterol., 2001, 96: 1977-1997

Non-patent Reference 4: Nucl. Med. Commun., 2005, 26: 649-655

Non-patent Reference 5: Saishin Igaku (Newest Medical Science), 2004, 59: 1070-1075

DISCLOSURE OF THE INVENTION

Problems that the Invention is to Solve

An object of the invention is to provide a therapeutic agent for inflammatory bowel disease comprising an amino alcohol derivative as an active ingredient or a method for treating inflammatory bowel disease.

Means for Solving the Problems

The present inventors have found that a specific amino alcohol derivative is useful in treating inflammatory bowel diseases (Crohn's disease, ulcerative colitis and the like) and thereby accomplished the invention.

Specifically, the invention relates to:
1) a therapeutic agent or prophylactic agent for inflammatory bowel disease, comprising as an active ingredient an amino alcohol derivative or a pharmaceutically acceptable salt or hydrate thereof, wherein the amino alcohol derivative is represented by the general formula (1),

[Chemical formula 1]

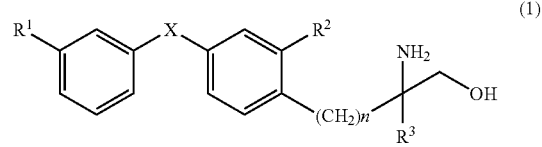

(1)

[wherein $R^1$ represents a chlorine atom or a straight-chain alkyl group having 1 to 3 carbon atoms or trifluoromethyl group, $R^2$ represents a fluorine atom or a chlorine atom, $R^3$ represents a straight-chain alkyl group having 1 to 3 carbon atoms, X represents an oxygen atom or a sulfur atom, and n denotes 2 or 3], 2) the therapeutic agent or prophylactic agent for inflammatory bowel disease, comprising as an active ingredient the amino alcohol derivative according to 1), or a pharmaceutically acceptable salt or hydrate thereof, wherein the compound represented by the general formula (1) is a compound represented by the general formula (1a),

[Chemical formula 2]

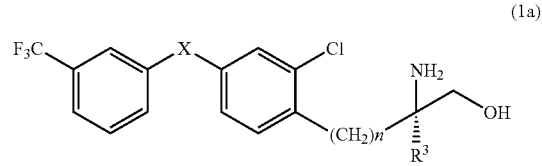

(1a)

[wherein $R^3$, X, and n are as described above], 3) the therapeutic agent or prophylactic agent for inflammatory bowel disease, comprising as an active ingredient the amino alcohol derivative according to 1) or 2), or a pharmaceutically acceptable salt or hydrate thereof, wherein in the general formula (1a), $R^3$ is a methyl group, 4) the therapeutic agent or prophylactic agent for inflammatory bowel disease, comprising as an active ingredient the amino alcohol derivative according to 1), or a pharmaceutically acceptable salt or hydrate thereof, wherein the compound represented by the general formula (1) is, (R)-2-amino-5-[2-chloro-4-(3-trifluoromethylphenoxy)phenyl]-2-methylpentan-1-ol, (R)-2-amino-5-[2-chloro-4-(3-trifluoromethylphenylthio) phenyl]-2-methylpentan-1-ol, (R)-2-amino-4-[2-chloro-4-(3-trifluoromethylphenoxy)phenyl]-2-methylbutan-1-01, (R)-2-amino-4-[2-chloro-4-(3-trifluoromethylphenylthio) phenyl]-2-methylbutan-1-ol, (R)-2-amino-5-[2-chloro-4-(3-ethylphenylthio)phenyl]-2-methylpentan-1-ol, (R)-2-amino-5-[2-fluoro-4-(3-trifluoromethylphenylthio) phenyl]-2-methylpentan-1-01, or (R)-2-amino-5-[2-chloro-4-(3-trifluoromethylphenylthio) phenyl]-2-propylpentan-1-ol, 5) a therapeutic agent or prophylactic agent for inflammatory bowel disease, comprising as an active ingredient an optically active amino alcohol derivative, or a pharmaceutically acceptable salt or hydrate thereof, being obtainable by a step of allowing a compound represented by the general formula (2),

[Chemical formula 3]

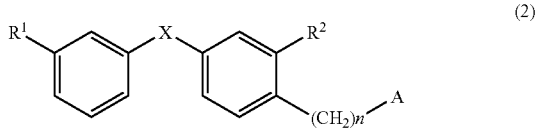

(2)

[wherein $R^1$ represents a chlorine atom or a straight-chain alkyl group having 1 to 3 carbon atoms or trifluoromethyl group, $R^2$ represents a fluorine atom or a chlorine atom, A represents a halogen atom, X represents an oxygen atom or a sulfur atom, and n denotes 2 or 3] and a compound represented by the general formula (10),

[Chemical formula 4]

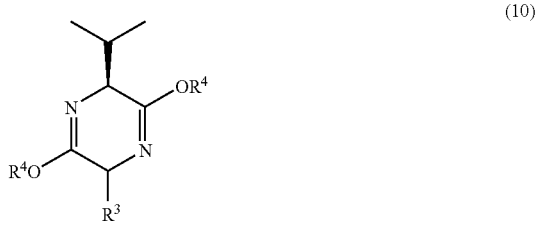

(10)

[wherein $R^3$ represents a straight-chain alkyl group having 1 to 3 carbon atoms and $R^4$ represents an alkyl group having 1 to 6 carbon atoms] to act in the presence of a base, and a step of subjecting the resultant product to acidolysis, then further protecting a nitrogen atom with a t-butoxycarbonyl group, reducing, and deprotecting the nitrogen atom], and 6) a method of treating or preventing inflammatory bowel disease, the method comprising administrating the amino alcohol derivative according to any one of 1) to 5), or a pharmaceutically acceptable salt or hydrate thereof

ADVANTAGE OF THE INVENTION

According to the invention, it became possible to provide a therapeutic agent or prophylactic agent for inflammatory bowel diseases (Crohn's disease, ulcerative colitis, intestinal Behcet's disease, hemorrhagic rectal ulcer, pouchitis and the like), which shows fewer side effects.

BEST MODE FOR CARRYING OUT THE INVENTION

In the present invention, the straight-chain alkyl group having 1 to 3 carbon atoms of $R^1$ and $R^3$ is a methyl group, an ethyl group, or an n-propyl group.

From the perspective of obtaining high safety, $R^1$ is preferably an ethyl group, a propyl group, or a trifluoromethyl group, and more preferably is a trifluoromethyl group. Furthermore, $R^3$ is preferably a methyl group, and n is preferably 3.

Furthermore, the configuration of $R^3$ is preferably a configuration produced as the principal product via the below-described synthesis route B (using the compound (10)).

In the present invention, examples of pharmaceutically acceptable salts include acid addition salts such as hydrochloride salts, hydrobromic acid salts, acetic acid salts, trifluoroacetic acid salts, methanesulfonic acid salts, citric acid salts, or tartaric acid salts.

The active ingredient of the therapeutic agent or prophylactic agent according to the present invention represented by the general formula (1) can be produced, for example, via the synthesis route A shown below.

<Synthesis Route A>

[Chemical formula 5]

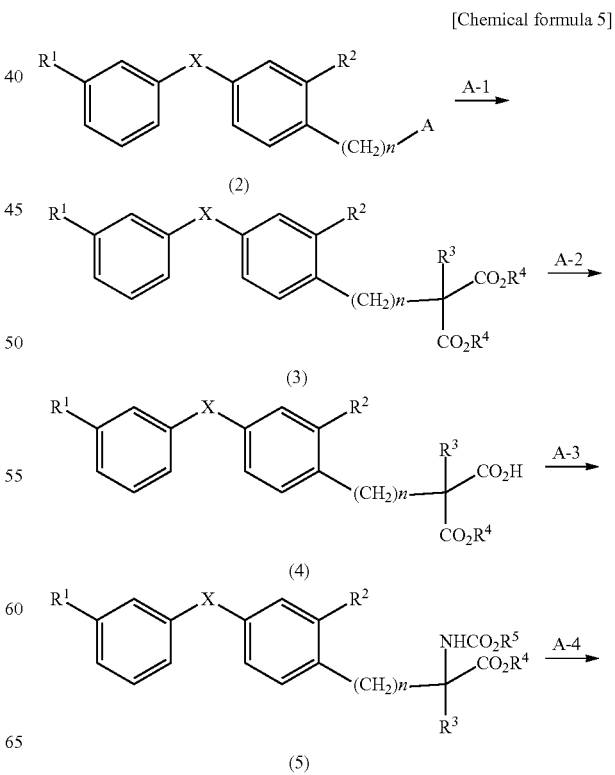

-continued

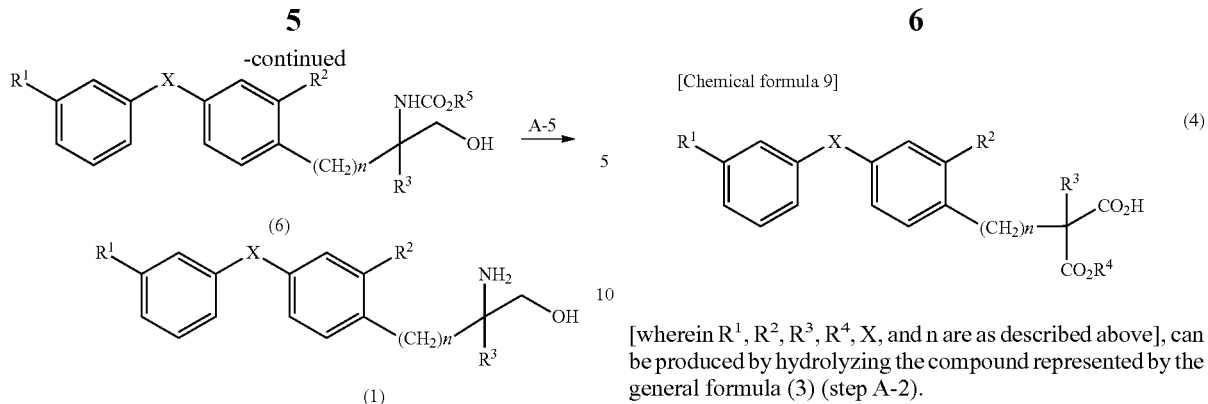

In the synthesis route A, the compound represented by the general formula (3),

[Chemical formula 6]

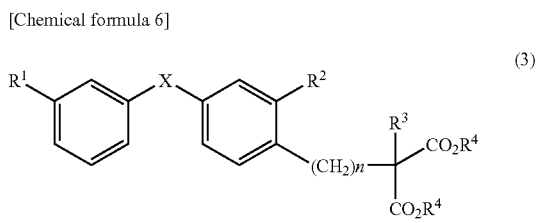

[wherein $R^1$, $R^2$, $R^3$, $R^4$, X and n are as described above], can be produced by allowing a compound represented by the general formula (2),

[Chemical formula 7]

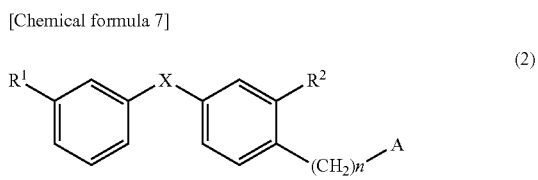

[wherein $R^1$, $R^2$, A, X, and n are as described above], and a compound represented by the general formula (7),

[Chemical formula 8]

[wherein $R^3$ and $R^4$ are as described above] to act in the presence of a base (step A-1).

The reaction can be carried out using methanol, ethanol, 1,4-dioxane, dimethylsulfoxide (DMSO), N,N-dimethylformamide (DMF), tetrahydrofuran (THF) or the like as a reaction solvent, in the presence of an inorganic base such as sodium hydride, potassium hydride, sodium methoxide, sodium ethoxide, sodium t-butoxide, potassium methoxide, potassium ethoxide, potassium t-butoxide, or potassium carbonate, at 0° C. to reflux temperature as the reaction temperature, and preferably at 80° C. to 100° C.

In the synthesis route A, the compound represented by the general formula (4),

[Chemical formula 9]

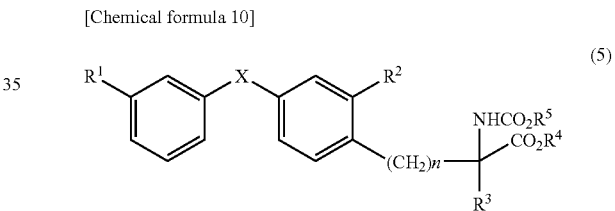

[wherein $R^1$, $R^2$, $R^3$, $R^4$, X, and n are as described above], can be produced by hydrolyzing the compound represented by the general formula (3) (step A-2).

The reaction can be carried out in the presence of a base such as aqueous sodium hydroxide, aqueous potassium hydroxide, or aqueous lithium hydroxide, using methanol, ethanol, 1,4-dioxane, DMF, DMSO, THF or the like as a reaction solvent, at a reaction temperature of 0° C. to reflux temperature. Preferably, the reaction is carried out using potassium hydroxide as the base, in an ethanol solvent, by reacting at 50° C.

Although the compound according to the present invention is preferably a specific optically-active substance, when the optical resolution is carried out is not especially limited. At this stage, optical resolution may be carried out by HPLC using a chiral column, whereby the desired compound having a chiral center can be obtained.

In the synthesis route A, the compound represented by the general formula (5),

[Chemical formula 10]

[wherein $R^5$ represents an alkyl group having 1 to 6 carbon atoms, and $R^1$, $R^2$, $R^3$, $R^4$, X, and n are as described above], can be produced by subjecting the compound represented by the general formula (4) to Curtius rearrangement (step A-3).

In the reaction, typical methods for converting a carboxyl group into a carbamate may be employed. For example, a method which combines, for example, chloroethyl carbonate and $NaN_3$, or oxalyl chloride and $NaN_3$, or a method which uses only diphenylphosphoryl azide (DPPA) may be utilized. The reaction is preferably carried out by, after heating diphenylphosphoryl azide to reflux in the presence of an organic base, such as triethylamine, in benzene or toluene solvent, charging the resultant product with an alcohol represented by the general formula (8), $$R^5OH \quad (8)$$

[herein $R^5$ is as described above], and continuing to heat the resultant solution under stirring, or, after removing the solvent used in the above reaction, such as benzene or toluene, by evaporation, by heating to reflux using the alcohol represented by the general formula (8) as a reaction solvent.

At this stage, optical resolution may be carried out by HPLC using a chiral column, whereby the desired compound having a chiral center can be obtained.

In the synthesis route A, the compound represented by the general formula (6),

[Chemical formula 11]

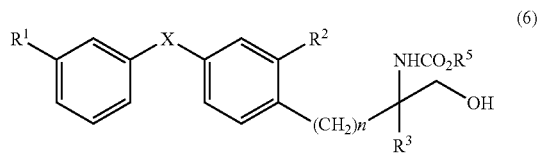
(6)

[wherein $R^1$, $R^2$, $R^3$, $R^5$, X, and n are as described above], can be produced by reducing the compound represented by the general formula (5) (step A-4).

The reaction can be carried out using borane, an alkyl borane derivative like 9-borabicyclo[3.3.1]nonane (9-BBN), or a metal hydride complex compound, such as diisobutylaluminum hydride ($(iBu)_2AlH$), sodium borohydride ($NaBH_4$), lithium borohydride ($LiBH_4$), and lithium aluminum hydride ($LiAlH_4$), preferably $LiBH_4$, using THF, 1,4-dioxane, ethanol, or methanol as a reaction solvent, at a temperature of 0° C. to reflux temperature, and preferably at room temperature.

Furthermore, at this stage also, optical resolution may be carried out by HPLC using a chiral column, whereby the desired compound having a chiral center can be obtained.

In the synthesis route A, the compound represented by the general formula (1) can be produced by subjecting the compound represented by the general formula (6) to acidolysis or hydrolysis (step A-5).

The reaction can be carried out at room temperature to reflux temperatures in an inorganic acid or organic acid, such as hydrochloric acid, hydrobromic acid, methanesulfonic acid, acetic acid, and trifluoroacetic acid, or at room temperature to reflux temperature by adding an organic solvent such as methanol, ethanol, THF, or 1,4-dioxane to an inorganic acid or organic acid, such as hydrochloric acid, hydrobromic acid, methanesulfonic acid, acetic acid, and trifluoroacetic acid. The reaction may also be carried out in the presence of a base such as aqueous sodium hydroxide, aqueous potassium hydroxide, and aqueous lithium hydroxide, using methanol, ethanol, THF, 1,4-dioxane, DMSO, or DMF as a reaction solvent, at a temperature of 0° C. to reflux temperature, and preferably 80 to 100° C.

In the synthesis route A, among the compounds represented by the general formula (5), compounds in which $R^5$ represents a t-butyl group, specifically, a compound represented by the general formula (5a),

[Chemical formula 12]

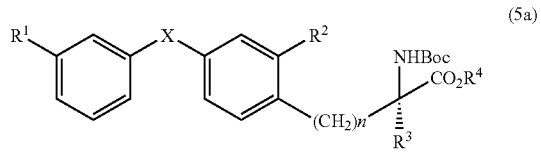
(5a)

[wherein Boc represents a t-butoxycarbonyl group, and $R^1$, $R^2$, $R^3$, $R^4$, X, and n are as described above], and among the compounds represented by the general formula (6) in the synthesis route A, compounds in which $R^5$ represents a t-butyl group, specifically, a compound represented by the general formula (6a),

[Chemical formula 13]

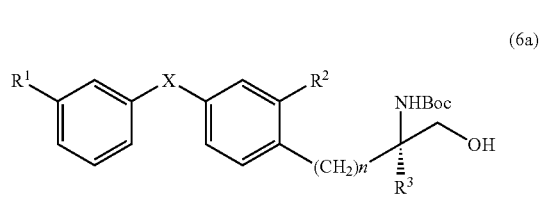
(6a)

[wherein $R^1$, $R^2$, $R^3$, X, Boc, and n are as described above], can be produced by the synthesis route B.

<Synthesis Route B>

[Chemical formula 14]

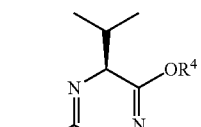
(10)

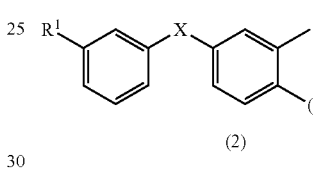
(2)
B-1 →

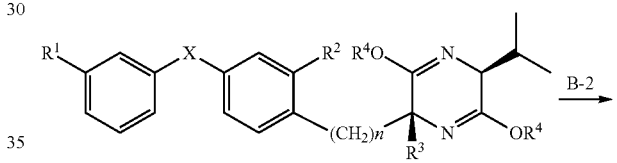
(9)
B-2 →

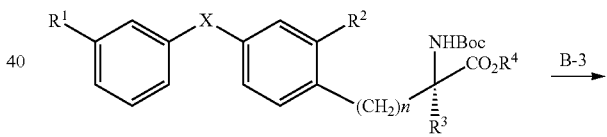
(5a)
B-3 →

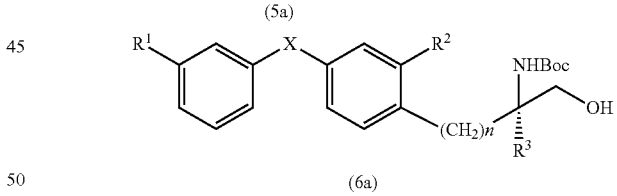
(6a)

In the synthesis route B, the compound represented by the general formula (9),

[Chemical formula 15]

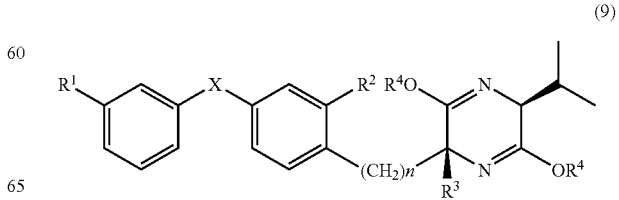
(9)

[wherein $R^1$, $R^2$, $R^3$, $R^4$, X, and n are as described above], can be produced by allowing a compound represented by the general formula (2) and a compound represented by the general formula (10),

[Chemical formula 16]

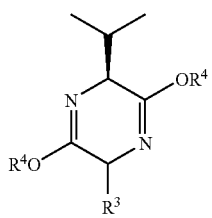

(10)

[wherein $R^3$ and $R^4$ are as described above] to react in the presence of a base (step B-1).

The reaction can be carried out using a reaction solvent such as 1,4-dioxane, THF, and ether, using a base such as n-butyllithium or lithium diisopropyl amide, preferably n-butyllithium, and treating a compound represented by the general formula (10) at −78° C., then allowing a compound represented by general formula (2) to react at −78° C., and reacting while gradually increasing the temperature to room temperature.

In the synthesis route B, the compound represented by the general formula (5a) can be produced by subjecting a compound represented by the general formula (9) to acidolysis, and then protecting the nitrogen atom with a t-butoxycarbonyl group (Boc group) (step B-2).

In the reaction, an amino ester can be obtained using methanol, ethanol, THF, 1,4-dioxane, or ethyl acetate in which hydrochloric acid is dissolved, and preferably 1,4-dioxane containing hydrochloric acid, by reacting at reflux temperature, then neutralizing with a base. Furthermore, it is preferred to allowing it to react with $Boc_2O$ at 0° C. to room temperature using ethyl acetate, THF, DMF, 1,4-dioxane, methylene chloride, chloroform, methanol, ethanol, acetonitrile or the like as a solvent.

In the synthesis route B, the compound represented by the general formula (6a) can be produced by reducing a compound represented by the general formula (5a) (step B-3).

The reaction can be carried out using borane, an alkyl borane derivative like 9-BBN, or a metal hydride complex compound, such as $(iBu)_2AlH$, $NaBH_4$, $LiBH_4$, and $LiAlH_4$, preferably $LiBH_4$, using THF, 1,4-dioxane, ethanol, or methanol as a reaction solvent, at a temperature of 0° C. to reflux temperature, and preferably at room temperature.

It is noted that concerning the synthesis method of the compound represented by the general formula (2), the compound may be produced by the methods described in the respective pamphlets of WO 03029184, WO 03029205, WO 04026817, WO 04074297, and WO 050444780.

The therapeutic agent or prophylactic agent for inflammatory bowel diseases, which comprises the compound obtained in this manner as an active ingredient, is systemically or topically administered orally or parenterally. Dosage form of the compound can be changed in response to the properties of the compound, and it is possible to be prepared as an oral preparation or a parenteral preparation. That is, granules, powders, tablets, capsules, syrups, suppositories, suspensions, solutions and the like can be prepared by mixing the active ingredient with physiologically acceptable carriers, fillers, binders, diluents and the like.

The inflammatory bowel disease according to the invention means enteritis which occurs in small intestine or large intestine, and Crohn's disease, ulcerative colitis, intestinal Behcet's disease, hemorrhagic rectal ulcer, pouchitis and the like can be exemplified.

As the clinical dose, though it changes depending on the body weight, age and the condition to be treated, it is generally from 0.01 to 100 mg, preferably from 0.1 to 5 mg, per one person as the amount per once, and from 1 to 3 times per day is convenient.

EXAMPLES

The present invention will be described with the following specific examples. However, the present invention is not limited by these examples.

Furthermore, as the intermediates and the like represented by the general formula (2), the compounds in the pamphlets of WO 03029184, WO 03029205, WO 04026817, WO 04074297, and WO 050444780 may be utilized. Furthermore, (5S)-3,6-diethoxy-5-isopropyl-2-methyl-2,5-dihydropyrazine, (5S)-3,6-dimethoxy-5-isopropyl-2-methyl-2,5-dihydropyrazine, and (5S)-2-allyl-3,6-diethoxy-5-isopropyl-2,5-dihydropyrazine were synthesized according to Ulrich Shollkopf et. al, Synthesis 969 (1981) and Chunrong Ma et. al., J. Org. Chem., 66, 4525 (2001). Intermediates and the like which were newly synthesized based on the experiment procedures described in these reference documents will now be described as the following reference examples.

Reference Example 1

2-Fluoro-4-(3-trifluoromethylphenylthio)benzaldehyde

[Chemical formula 17]

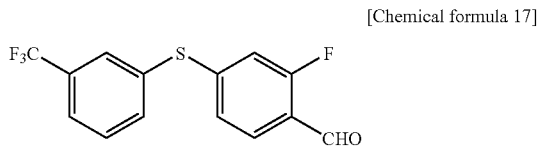 [SMILES: O=Cc1ccc(Sc2cccc(C(F)(F)F)c2)cc1F]

Under an argon atmosphere, ethyldiisopropylamine (7.0 mL), tris(dibenzylideneacetone)dipalladium(0) chloroform adduct (518 mg), xantphos (578 mg), and 3-trifluoromethylthiophenol (3.56 g) were added at room temperature into a solution of 4-bromo-2-fluorobenzaldehyde (4.06 g) in 1,4-dioxane (42 mL), and the resultant solution was heated to reflux for 5 hours. To the reaction solution added water, extracted with ethyl acetate, washed with water and saturated brine in that order, and then dried over anhydrous sodium sulfate. The solvent was evaporated, and the resultant residue was purified by silica gel column chromatography (hexane: ethyl acetate=30:1) to obtain the target product (4.08 g) as a colorless oil.

$^1$H-NMR ($CDCl_3$, 400 MHz): δ 6.86 (1H, dd, J=10, 1.8 Hz), 7.02 (1H, dd, J=7.9, 1.8 Hz), 7.58 (1H, t, J=7.9 Hz), 7.68-7.73 (2H, m), 7.76 (1H, t, J=7.9 Hz), 7.80 (1H, s), 10.26 (1H, s)

EIMS (+): 300 $[M]^+$.

Reference Example 2

2-Chloro-4-(3-chlorophenylthio)benzaldehyde

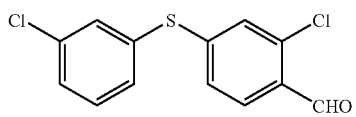

[Chemical formula 18]

3-Chlorobenzenethiol and 2-chloro-4-fluorobenzaldehyde were reacted according to the same experiment procedures as in Reference Example 1 of the pamphlet of WO 03029205 to obtain the target product as a colorless oil.

$^1$H-NMR (CDCl$_3$, 400 MHz): δ 7.11 (1H, dd, J=9.2, 1.8 Hz), 7.17 (1H, d, J=1.8 Hz), 7.36-7.44 (3H, m), 7.52 (1H, t, J=1.8 Hz), 7.80 (1H, d, J=7.9 Hz), 10.37 (1H, s)

EIMS (+): 282 [M]$^+$.

Reference Example 3

2-Chloro-4-(3-methylphenoxy)benzaldehyde

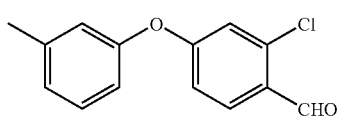

[Chemical formula 19]

m-Cresol and 2-chloro-4-fluorobenzaldehyde were reacted according to the same experiment procedures as in Reference Example 1 of the pamphlet of WO 03029184 to obtain the target product as a colorless powder.

$^1$H-NMR (CDCl$_3$, 400 MHz): δ 2.38 (3H, s), 6.87-6.96 (4H, m), 7.07 (1H, d, J=7.3 Hz), 7.31 (1H, t, J=7.6 Hz), 7.90 (1H, d, J=8.6 Hz), 10.36 (1H, s).

EIMS (+): 246 [M]$^+$.

Reference Example 4

2-Chloro-4-(3-ethylphenylthio)benzaldehyde

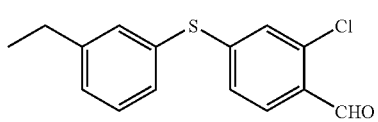

[Chemical formula 20]

3-Ethylbenzenethiol and 2-chloro-4-fluorobenzaldehyde were reacted according to the same experiment procedures as in Reference Example 1 of the pamphlet of WO 03029205 to obtain the target product as a colorless oil.

$^1$H-NMR (CDCl$_3$, 400 MHz): δ 1.26 (3H, t, J=7.3 Hz), 2.68 (2H, q, J=7.3 Hz), 7.04-7.11 (2H, m), 7.28-7.40 (4H, m), 7.76 (1H, d, J=8.6 Hz), 10.35 (1H, s).

EIMS (+): 276 [M]$^+$.

Reference Example 5

2-Chloro-4-(3-propylphenoxy)benzaldehyde

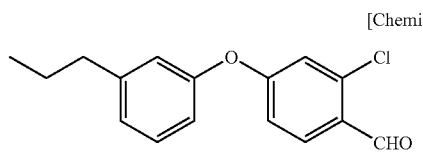

[Chemical formula 21]

3-Propylphenol and 2-chloro-4-fluorobenzaldehyde were reacted according to the same experiment procedures as in Reference Example 1 of the pamphlet of WO 03029184 to obtain the target product as a pale brown oil.

$^1$H-NMR (CDCl$_3$, 400 MHz): δ 0.95 (3H, t, J=7.3 Hz), 1.62-1.68 (2H, m), 2.61 (2H, t, J=7.3 Hz), 6.89-6.94 (3H, m), 6.96 (1H, d, J=2.1 Hz), 7.08 (1H, d, J=7.9 Hz), 7.31-7.35 (1H, m), 7.90 (1H, d, J=8.9 Hz), 10.36 (1H, d, J=0.6 Hz).

EIMS (+): 274 [M]$^+$.

Reference Example 6

[2-Chloro-4-(3-ethylphenylthio)phenyl]acetaldehyde

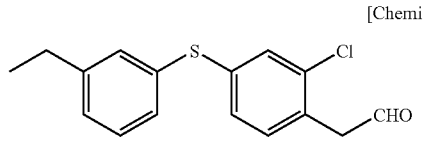

[Chemical formula 22]

The compound of Reference Example 4 was reacted according to the same experiment procedures as in Reference Example 326 of the pamphlet of WO 04074297 to obtain the target product as a pale yellow oil.

Reference Example 7

Ethyl 3-[2-chloro-4-(3-ethylphenylthio)phenyl]acrylate

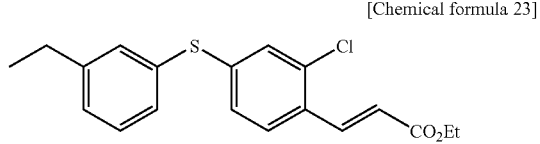 [SMILES: CCOC(=O)C=Cc1ccc(Sc2cccc(CC)c2)cc1Cl]

[Chemical formula 23]

The compound of Reference Example 4 was reacted according to the same experiment procedures as in Reference Example 10 of the pamphlet of WO 03029205 to obtain the target product as a pale yellow oil.

EIMS (+): 346 [M]$^+$.

Reference Example 8

3-[2-Chloro-4-(3-ethylphenylthio)phenyl]propan-1-ol

[Chemical formula 24]

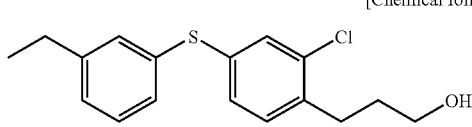

The compound of Reference Example 7 was reacted according to the same experiment procedures as in Reference Example 19 of the pamphlet of WO 03029205, and the resultant product was then reduced according to the same experiment procedures as in Reference Example 35 of the pamphlet of WO 03029205, to obtain the target product as a colorless oil.

$^{1}$H-NMR (CDCl$_{3}$, 400 MHz,): δ 1.22 (3H, t, J=7.3 Hz), 1.84-1.90 (2H, m), 2.62 (2H, q, J=7.6 Hz), 2.78-2.82 (2H, m), 3.69 (2H, t, J=6.1 Hz), 7.10-7.18 (4H, m), 7.23-7.29 (3H, m).

Reference Example 9

3-[2-Chloro-4-(3-propylphenoxy)phenyl]propan-1-ol

[Chemical formula 25]

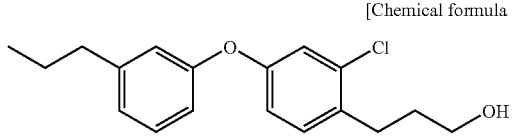

The compound of Reference Example 5 was successively reacted according to the same procedures as in Reference Example 7 and then Reference Example 8 to obtain the target product as a colorless oil.

$^{1}$H-NMR (CDCl$_{3}$, 400 MHz,): δ 0.94 (3H, t, J=7.3 Hz), 1.37 (1H, br s), 1.58-1.68 (2H, m), 1.85-1.92 (2H, m), 2.57 (2H, t, J=7.6 Hz), 2.80 (2H, t, J=7.6 Hz), 3.70 (2H, dt, J=6.1, 4.6 Hz), 6.80-6.85 (3H, m), 6.95 (1H, d, J=7.9 Hz), 7.00 (1H, d, J=2.8 Hz), 7.17 (1H, d, J=8.3 Hz), 7.24 (1H, t, J=7.9 Hz).
EIMS (+): 304 [M]$^{+}$.

Reference Example 10

3-[2-Fluoro-4-(3-trifluoromethylphenylthio)phenyl]propan-1-ol

[Chemical formula 26]

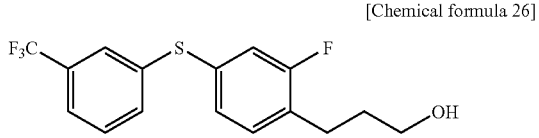 [SMILES: OCCCc1ccc(Sc2cccc(C(F)(F)F)c2)cc1F]

The compound of Reference Example 1 was successively reacted according to the same procedures as in Reference Example 7 and then Reference Example 8 to obtain the target product as a colorless oil.

$^{1}$H-NMR (CDCl$_{3}$, 400 MHz): δ 1.88 (2H, tt, J=6.7, 6.1 Hz), 2.75 (2H, t, J=6.7 Hz), 3.69 (2H, t, J=6.1 Hz), 7.05 (1H, dd, J=10, 1.8 Hz), 7.10 (1H, dd, J=7.9, 1.8 Hz), 7.20 (1H, t, J=7.9 Hz), 7.38-7.51 (3H, m), 7.55 (1H, s).

Reference Example 11

3-[2-Chloro-4-(3-chlorophenylthio)phenyl]propan-1-ol

[Chemical formula 27]

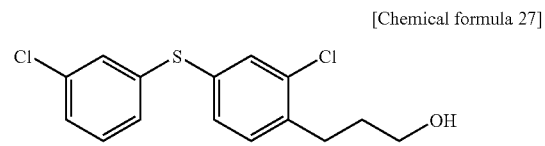 [SMILES: OCCCc1ccc(Sc2cccc(Cl)c2)cc1Cl]

The compound of Reference Example 2 was successively reacted according to the same procedures as in Reference Example 7 and then Reference Example 8 to obtain the target product as a colorless oil.

$^{1}$H-NMR (CDCl$_{3}$, 400 MHz): δ 1.33 (1H, br s), 1.83-1.95 (2H, m), 2.81-2.85 (2H, m), 3.70 (2H, br s), 7.15-7.23 (5H, m), 7.24-7.29 (1H, m), 7.38 (1H, d, J=1.8 Hz).

Reference Example 12

3-[2-Chloro-4-(3-methylphenoxy)phenyl]propan-1-ol

[Chemical formula 28]

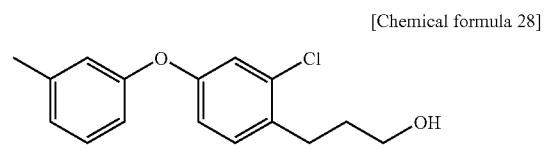 [SMILES: Cc1cccc(Oc2ccc(CCCO)c(Cl)c2)c1]

The compound of Reference Example 3 was successively reacted according to the same procedures as in Reference Example 7 and then Reference Example 8 to obtain the target product as a colorless oil.

$^{1}$H-NMR (CDCl$_{3}$, 400 MHz): δ 1.31 (1H, brs), 1.87-1.90 (2H, m), 2.34 (3H, s), 2.80 (2H, t, J=7.3 Hz), 3.70 (2H, dd, J=11.6, 6.1 Hz), 6.79-6.86 (3H, m), 6.94 (1H, d, J=7.3 Hz), 6.99 (1H, d, J=2.4 Hz), 7.18 (1H, d, J=7.9 Hz), 7.22 (1H, t, J=7.3 Hz).
EIMS (+): 276 [M]$^{+}$.

Reference Example 13

2-Chloro-4-(3-ethylphenylthio)-1-(2-iodoethyl)benzene

[Chemical formula 29]

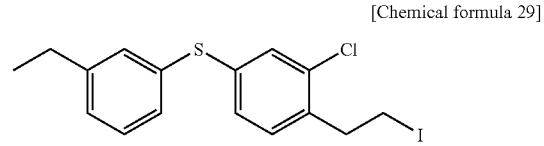 [SMILES: CCc1cccc(Sc2ccc(CCI)c(Cl)c2)c1]

The compound of Reference Example 6 was reacted according to the same experiment procedures as in Reference Example 327 of the pamphlet of WO 04074297 to obtain the target product as a colorless oil.

$^1$H-NMR (CDCl$_3$, 400 MHz): δ 1.22 (3H, t, J=7.3 Hz), 2.63 (2H, q, J=7.3 Hz), 3.23-3.28 (2H, m), 3.32-3.35 (2H, m), 7.09-7.29 (7H, m).

EIMS (+): 402 [M]$^+$.

Reference Example 14

2-Chloro-4-(3-ethylphenylthio)-1-(3-iodopropyl) benzene

[Chemical formula 30]

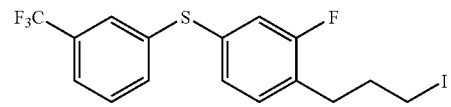

The compound of Reference Example 8 was reacted according to the same experiment procedures as in Reference Example 164 of the pamphlet of WO 03029184 to obtain the target product as a colorless oil.

$^1$H-NMR (CDCl$_3$, 400 MHz): δ 1.22 (3H, t, J=7.3 Hz), 2.12 (2H, quintet, J=7.3 Hz), 2.63 (2H, q, J=7.3 Hz), 2.81 (2H, t, J=7.3 Hz), 3.19 (2H, t, J=7.3 Hz), 7.09-7.19 (4H, m), 7.24-7.28 (3H, m).

EIMS (+): 416 [M]$^+$.

Reference Example 15

2-Chloro-1-(3-iodopropyl)-4-(3-propylphenoxy) benzene

[Chemical formula 31]

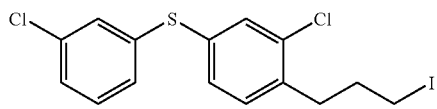

The compound of Reference Example 9 was reacted according to the same experiment procedures as in Reference Example 164 of the pamphlet of WO 03029184 to obtain the target product as a pale yellow oil.

$^1$H-NMR (CDCl$_3$, 400 MHz): δ 0.94 (3H, t, J=7.3 Hz), 1.60-1.68 (2H, m), 2.10-2.17 (2H, m), 2.57 (2H, t, J=7.6 Hz), 2.81 (2H, t, J=7.6 Hz), 3.21 (2H, t, J=7.0 Hz), 6.80-6.85 (3H, m), 6.96 (1H, d, J=7.9 Hz), 6.99 (1H, d, J=2.4 Hz), 7.19 (1H, d, J=8.3 Hz), 7.25 (1H, t, J=7.9 Hz).

EIMS (+): 414 [M]

Reference Example 16

2-Fluoro-1-(3-iodopropyl)-4-(3-trifluoromethylphenylthio)benzene

[Chemical formula 32]

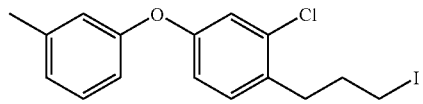

The compound of Reference Example 10 was reacted according to the same experiment procedures as in Reference Example 164 of the pamphlet of WO 03029184 to obtain the target product as a colorless oil.

$^1$H-NMR (CDCl$_3$, 400 MHz): δ 2.13 (2H, quintet, J=7.3 Hz), 2.76 (2H, t, J=7.3 Hz), 3.18 (2H, t, J=6.7 Hz), 7.03 (1H, dd, J=10, 1.8 Hz), 7.09 (1H, dd, J=7.9, 1.8 Hz), 7.20 (1H, t, J=7.9 Hz), 7.39-7.52 (3H, m), 7.57 (1H, s).

EIMS (+): 404 [M]$^+$.

Reference Example 17

2-Chloro-4-(3-chlorophenylthio)-1-(3-iodopropyl) benzene

[Chemical formula 33]

The compound of Reference Example 11 was reacted according to the same experiment procedures as in Reference Example 164 of the pamphlet of WO 03029184 to obtain the target product as a colorless oil.

$^1$H-NMR (CDCl$_3$, 400 MHz): δ 2.14 (2H, tt, J=7.3, 6.7 Hz), 2.84 (2H, t, J=7.3 Hz), 3.20 (2H, t, J=6.7 Hz), 7.16-7.25 (5H, m), 7.28 (1H, t, J=1.8 Hz), 7.36 (1H, d, J=1.8 Hz).

EIMS (+): 422 [M]$^+$.

Reference Example 18

2-Chloro-1-(3-iodopropyl)-4-(3-methylphenoxy) benzene

[Chemical formula 34]

The compound of Reference Example 12 was reacted according to the same experiment procedures as in Reference Example 164 of the pamphlet of WO 03029184 to obtain the target product as a yellow oil.

$^1$H-NMR (CDCl$_3$, 400 MHz): δ 2.13 (2H, quint, J=7.3 Hz), 2.34 (3H, s), 2.81 (2H, t, J=7.3 Hz), 3.21 (2H, t, J=7.3 Hz), 6.81-6.84 (3H, m), 6.95 (1H, d, J=7.9 Hz), 6.99 (1H, d, J=2.4 Hz), 7.18 (1H, d, J=7.9 Hz), 7.23 (1H, t, J=7.9 Hz).
EIMS (+): 386 [M]$^+$.

Example 1

(2R,5S)-2-[2-chloro-4-(3-trifluoromethylphenoxy)phenyl]propyl-3,6-diethoxy-5-isopropyl-2-methyl-2,5-dihydropyrazine

[Chemical formula 35]

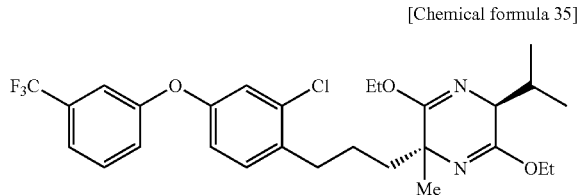 [SMILES: CCOC1=N[C@](C)(CCCc2ccc(Oc3cccc(C(F)(F)F)c3)cc2Cl)C(OCC)=N[C@H]1C(C)C]

Under an argon atmosphere, a solution of n-butyllithium in hexane (1.54 mol/L, 3.59 mL) was added at −78° C. into a solution of (5S)-3,6-diethoxy-5-isopropyl-2-methyl-2,5-dihydropyrazine (905 mg) in THF (16 mL), and the resultant solution was stirred at −78° C. for 30 minutes. Next, A solution of 2-chloro-1-(3-iodopropyl)-4-(3-trifluoromethylphenoxy)benzene (2.47 g) in THF (4 mL) was added to the reaction mixture, and the resultant solution was stirred at −78° C. for 30 minutes and then at 0° C. for 1 hour. To the reaction solution was added water, extracted with ethyl acetate, washed with water and saturated brine in that order, and then dried over anhydrous sodium sulfate. The solvent was evaporated, and the resultant residue was purified by silica gel column chromatography (hexane:ethyl acetate=60:1) to obtain the target product (1.59 g) as a colorless oil.

$^1$H-NMR (CDCl$_3$, 400 MHz): δ 0.70 (3H, d, J=6.7 Hz), 1.05 (3H, d, J=6.7 Hz), 1.18-1.50 (9H, m), 1.32 (3H, s), 1.86-1.97 (1H, m), 2.21-2.30 (1H, m), 2.65 (2H, t, J=7.6 Hz), 3.90 (1H, d, J=2.1 Hz), 3.97-4.21 (4H, m), 6.84 (1H, dd, J=7.9, 2.4 Hz), 7.00 (1H, d, J=2.4 Hz), 7.15 (2H, d, J=7.9 Hz), 7.24 (1H, br s), 7.36 (1H, d, J=7.9 Hz), 7.44 (1H, t, J=7.9 Hz).

Example 2

(2R,5S)-2-[2-chloro-4-(3-trifluoromethylphenylthio)phenyl]propyl-3,6-diethoxy-5-isopropyl-2-methyl-2,5-dihydropyrazine

[Chemical formula 36]

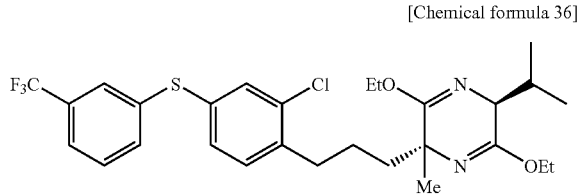

(5S)-3,6-diethoxy-5-isopropyl-2-methyl-2,5-dihydropyrazine and 2-chloro-1-(3-iodopropyl)-4-(3-trifluoromethylphenylthio)benzene were reacted in the same manner as in Example 1 to obtain the target product as a colorless oil.

$^1$H-NMR (CDCl$_3$, 400 MHz): δ 0.63 (3H, d, J=6.7 Hz), 1.07 (3H, d, J=6.7 Hz), 1.18-1.29 (10H, m), 1.34-1.66 (2H, m), 1.79-1.91 (1H, m), 2.25-2.33 (1H, m), 2.70 (2H, t, J=7.6 Hz), 3.85 (1H, br s), 3.99-4.23 (4H, m), 7.16 (2H, d, J=7.9 Hz), 7.20 (1H, dd, J=7.9, 1.8 Hz), 7.36-7.42 (3H, m), 7.44-7.50 (1H, m), 7.52 (1H, br s).

Example 3

(2R,5S)-2-[2-chloro-4-(3-trifluoromethylphenoxy)phenyl]ethyl-3,6-diethoxy-5-isopropyl-2-methyl-2,5-dihydropyrazine

[Chemial formula 37]

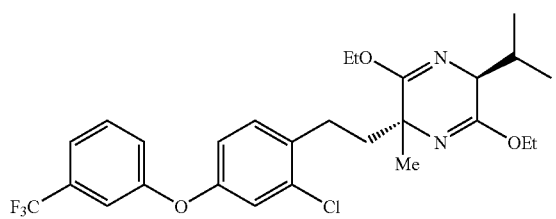

(5S)-3,6-diethoxy-5-isopropyl-2-methyl-2,5-dihydropyrazine and 2-chloro-1-(2-iodoethyl)-4-(3-trifluoromethylphenoxy)benzene were reacted in the same manner as in Example 1 to obtain the target product as a colorless oil.

$^1$H-NMR (CDCl$_3$, 400 MHz): δ 0.72 (3H, d, J=6.7 Hz), 1.08 (3H, d, J=6.7 Hz), 1.29 (6H, t, J=7.3 Hz), 1.36 (3H, s), 1.74-1.82 (1H, m), 2.13-2.20 (1H, m), 2.25-2.32 (1H, m), 2.39-2.56 (2H, m), 3.95 (1H, d, J=3.1 Hz), 4.02-4.22 (4H, m), 6.83 (1H, dd, J=8.6, 2.4 Hz), 6.99 (1H, d, J=2.4 Hz), 7.12-7.15 (2H, m), 7.23 (1H, br s), 7.35 (1H, d, J=7.8 Hz), 7.44 (1H, t, J=7.8 Hz).

EIMS (+): 524 [M]$^+$.

Example 4

(2R,5S)-2-[2-chloro-4-(3-trifluoromethylphenylthio)phenyl]ethyl-3,6-diethoxy-5-isopropyl-2-methyl-2,5-dihydropyrazine

[Chemial formula 38]

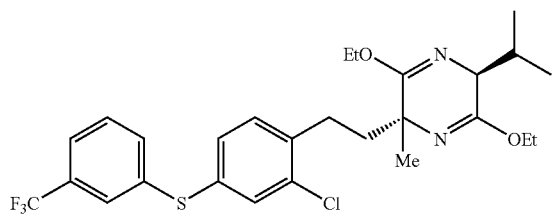

(5S)-3,6-diethoxy-5-isopropyl-2-methyl-2,5-dihydropyrazine and 2-chloro-1-(2-iodoethyl)-4-(3-trifluoromethylphenylthio)benzene were reacted in the same manner as in Example 1 to obtain the target product as a colorless oil.

$^1$H-NMR (CDCl$_3$, 400 MHz): δ 0.72 (3H, d, J=6.7 Hz), 1.08 (3H, d, J=6.7 Hz), 1.28 (6H, t, J=7.3 Hz), 1.35 (3H, s), 1.68-1.90 (1H, m), 2.10-2.19 (1H, m), 2.38-2.57 (1H, m), 3.95 (1H, d, J=3.1 Hz), 4.02-4.22 (4H, m), 7.13 (1H, d, J=7.9 Hz), 7.18 (1H, dd, J=7.9, 2.4 Hz), 7.35-7.42 (3H, m), 7.43-7.48 (1H, m), 7.54 (1H, br s).

Example 5

(2R,5S)-2-[2-chloro-4-(3-ethylphenylthio)phenyl]ethyl-3,6-diethoxy-5-isopropyl-2-methyl-2,5-dihydropyrazine

[Chemical formula 39]

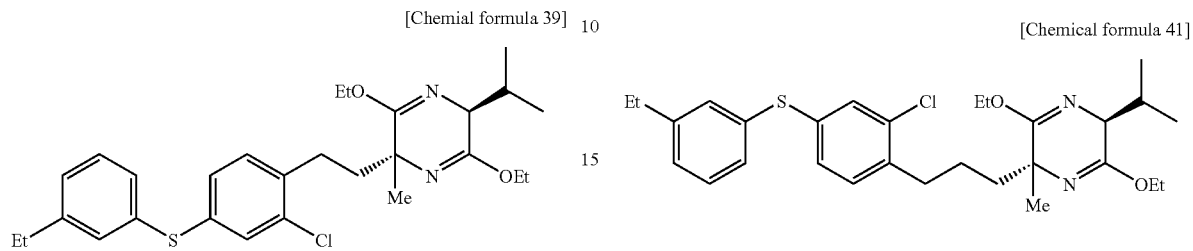

(5S)-3,6-diethoxy-5-isopropyl-2-methyl-2,5-dihydropyrazine and the compound of Reference Example 13 were reacted in the same manner as in Example 1 to obtain the target product as a colorless oil.

$^1$H-NMR (CDCl$_3$, 400 MHz): δ 0.72 (3H, d, J=6.7 Hz), 1.07 (3H, d, J=6.7 Hz), 1.21 (3H, t, J=7.3 Hz), 1.28 (3H, t, J=7.3 Hz), 1.29 (3H, t, J=7.3 Hz), 1.34 (3H, s), 1.70-1.79 (1H, m), 2.09-2.16 (1H, m), 2.24-2.32 (1H, m), 2.35-2.52 (2H, m), 2.61 (2H, q, J=7.3 Hz), 3.95 (1H, d, J=3.1 Hz), 4.03-4.20 (4H, m), 7.04-7.15 (4H, m), 7.21-7.26 (3H, m).

ESIMS (+): 501 [M+H]$^+$.

Example 6

(2R,5S)-2-[2-chloro-4-(3-methylphenoxy)phenyl]propyl-3,6-dimethoxy-5-isopropyl-2-methyl-2,5-dihydropyrazine

[Chemical formula 40]

(5S)-3,6-dimethoxy-5-isopropyl-2-methyl-2,5-dihydropyrazine and the compound of Reference Example 18 were reacted in the same manner as in Example 1 to obtain the target product as a colorless oil.

$^1$H-NMR (CDCl$_3$, 400 MHz): δ 0.68 (3H, d, J=6.7 Hz), 1.07 (3H, d, J=6.7 Hz), 1.33 (3H, s), 1.36-1.43 (1H, m), 1.55-1.62 (1H, m), 1.86-1.92 (1H, m), 2.24-2.26 (1H, m), 2.34 (3H, s), 2.62 (2H, t, J=7.9 Hz), 3.65 (3H, s), 3.66 (3H, s), 3.94 (1H, d, J=3.7 Hz), 6.79-6.82 (3H, m), 6.93 (1H, d, J=7.3 Hz), 6.96 (1H, d, J=2.4 Hz), 7.09 (1H, d, J=7.9 Hz), 7.22 (1H, t, J=7.9 Hz).

EIMS (+): 456 [M]$^+$.

Example 7

(2R,5S)-2-[2-chloro-4-(3-ethylphenylthio)phenyl]propyl-3,6-diethoxy-5-isopropyl-2-methyl-2,5-dihydropyrazine

[Chemical formula 41]

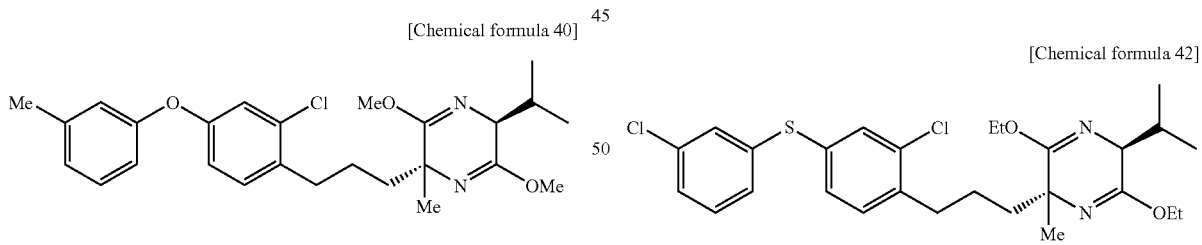

(5S)-3,6-diethoxy-5-isopropyl-2-methyl-2,5-dihydropyrazine and the compound of Reference Example 14 were reacted in the same manner as in Example 1 to obtain the target product as a colorless oil.

$^1$H-NMR (CDCl$_3$, 400 MHz): δ 0.68 (3H, d, J=6.7 Hz), 1.04 (3H, d, J=6.7 Hz), 1.20-1.26 (9H, m), 1.31 (3H, s), 1.36-1.43 (1H, m), 1.50-1.57 (1H, m), 1.85-1.92 (1H, m), 2.21-2.28 (1H, m), 2.60-2.65 (4H, m), 3.88 (1H, d, J=3.7 Hz), 4.00-4.16 (4H, m), 7.06-7.16 (4H, m), 7.22-7.27 (3H, m).

ESIMS (+): 515 [M+H]$^+$.

Example 8

(2R,5S)-2-[2-chloro-4-(3-chlorophenylthio)phenyl]propyl-3,6-diethoxy-5-isopropyl-2-methyl-2,5-dihydropyrazine

[Chemical formula 42]

(5S)-3,6-diethoxy-5-isopropyl-2-methyl-2,5-dihydropyrazine and the compound of Reference Example 17 were reacted in the same manner as in Example 1 to obtain the target product as a colorless oil.

$^1$H-NMR (CDCl$_3$, 400 MHz): δ 0.69 (3H, d, J=6.7 Hz), 1.08 (3H, d, J=6.7 Hz), 1.18-1.29 (7H, m), 1.31 (3H, s), 1.34-1.47 (1H, m), 1.50-1.63 (1H, m), 1.85-1.95 (1H, m), 2.20-2.30 (1H, m), 2.65 (2H, t, J=7.6 Hz), 3.89 (1H, d, J=3.1 Hz), 3.99-4.23 (4H, m), 7.11-7.23 (6H, m), 7.35 (1H, d, J=1.8 Hz).

ESIMS (+): 521 [M+H]$^+$.

Example 9

(2R,5S)-2-[2-fluoro-4-(3-trifluoromethylphenylthio)phenyl]propyl-3,6-diethoxy-5-isopropyl-2-methyl-2,5-dihydropyrazine

[Chemical formula 43]

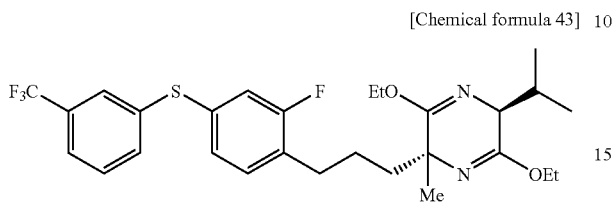

(5S)-3,6-diethoxy-5-isopropyl-2-methyl-2,5-dihydropyrazine and the compound of Reference Example 16 were reacted in the same manner as in Example 1 to obtain the target product as a colorless oil.

$^1$H-NMR (CDCl$_3$, 400 MHz): δ 0.67 (3H, d, J=6.7 Hz), 1.06 (3H, d, J=6.7 Hz), 1.18-1.29 (7H, m), 1.33 (3H, s), 1.36-1.66 (2H, m), 1.85-1.95 (1H, m), 2.23-2.33 (1H, m), 2.67 (2H, t, J=7.6 Hz), 3.89 (1H, d, J=3.1 Hz), 3.99-4.23 (4H, m), 7.02 (1H, dd, J=9.8 Hz, 1.8 Hz), 7.08 (1H, dd, J=7.9 Hz, 2.4 Hz), 7.13 (1H, t, J=7.9 Hz), 7.38-7.50 (3H, m), 7.55 (1H, s).

Example 10

(2S,5S)-2-allyl-2-[2-chloro-4-(3-trifluoromethylphenylthio)phenyl]propyl-3,6-diethoxy-5-isopropyl-2,5-dihydropyrazine

[Chemical formula 44]

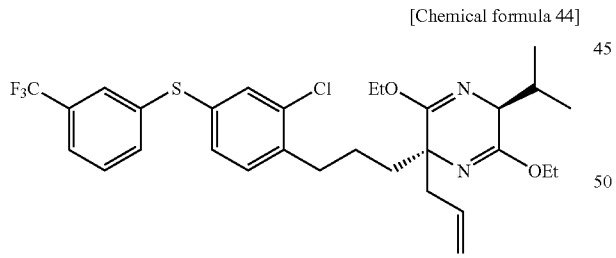

(5S)-2-allyl-3,6-diethoxy-5-isopropyl-2,5-dihydropyrazine and 2-chloro-1-(3-iodopropyl)-4-(3-trifluoromethylphenylthio)benzene were reacted in the same manner as in Example 1 to obtain the target product as a colorless oil.

$^1$H-NMR (CDCl$_3$, 400 MHz): δ 0.67 (3H, d, J=6.7 Hz), 1.05 (3H, d, J=6.7 Hz), 1.23 (3H, t, J=6.4 Hz), 1.25 (3H, t, J=6.4 Hz), 1.30-1.64 (3H, m), 1.80-1.90 (1H, m), 2.23-2.39 (2H, m), 2.53 (1H, dd, J=12.4, 7.3 Hz), 2.65 (2H, t, J=7.6 Hz), 3.83 (1H, d, J=3.1 Hz), 4.03-4.18 (4H, m), 4.92-5.04 (2H, m), 5.60-5.73 (1H, m), 7.13 (2H, d, J=7.9 Hz), 7.18 (1H, dd, J=7.9 Hz, 1.8 Hz), 7.36 (1H, d, J=1.8 Hz), 7.38-7.42 (2H, m), 7.44-7.49 (1H, m), 7.55 (1H, br s).

Example 11

Ethyl(R)-2-t-butoxycarbonylamino-5-[2-chloro-4-(3-trifluoromethylphenoxy)phenyl]-2-methylpentanoate

[Chemical formula 45]

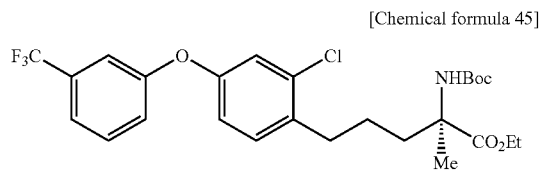

To a solution of the compound of Example 1 (1.59 g) in 1,4-dioxane (60 mL) was added 0.5 mol/L hydrochloric acid (30 mL). The resultant solution was stirred at room temperature for 1 hour, and then left to stand at room temperature overnight. The solution was concentrated, neutralized with saturated aqueous sodium hydrogen carbonate solution, and extracted with ethyl acetate. The extract was washed with water and saturated brine, and then dried over anhydrous sodium sulfate. The extract was concentrated, and the resultant residue was dissolved in acetonitrile (15 mL). To this solution was added di-tert-butoxydicarbonate (1.55 g), and the resultant solution was stirred at room temperature for 4 hours and then left to stand at room temperature overnight. To the reaction solution added water, extracted with ethyl acetate, washed with water and saturated brine in that order, and then dried over anhydrous sodium sulfate. The solvent was evaporated, and the resultant residue was purified by silica gel column chromatography (hexane:ethyl acetate=9:1) to obtain the target product (1.00 g) as a colorless oil.

$^1$H-NMR (CDCl$_3$, 400 MHz): δ 1.26 (3H, t, J=7.3 Hz), 1.43 (9H, s), 1.53 (3H, s), 1.45-1.68 (2H, m), 1.80-1.90 (1H, m), 2.12-2.30 (1H, m), 2.69 (2H, t, J=7.6 Hz), 4.16-4.24 (2H, m), 5.33 (1H, br s), 6.85 (1H, dd, J=7.9 Hz, 2.4 Hz), 7.02 (1H, d, J=2.4 Hz), 7.15 (1H, dd, J=7.9 Hz, 2.4 Hz), 7.17 (1H, d, J=7.9 Hz), 7.24 (1H, br s), 7.37 (1H, d, J=7.9 Hz), 7.45 (1H, t, J=7.9 Hz).

Example 12

Ethyl(R)-2-t-butoxycarbonylamino-5-[2-fluoro-4-(3-trifluoromethylphenylthio)phenyl]-2-methylpentanoate

[Chemical formula 46]

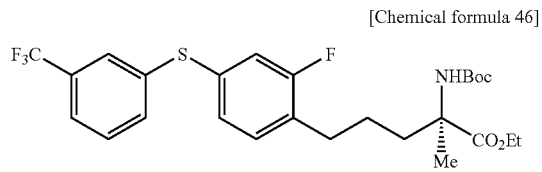

The compound of Example 9 was reacted in the same manner as in Example 11 to obtain the target product as a colorless oil.

$^1$H-NMR (CDCl$_3$, 400 MHz): δ 1.26 (3H, t, J=7.3 Hz), 1.42 (9H, s), 1.51 (3H, s), 1.45-1.68 (2H, m), 1.77-1.86 (1H, m), 2.09-2.20 (1H, m), 2.69 (2H, t, J=7.6 Hz), 4.13-4.23 (2H, m), 5.29 (1H, br s), 7.02 (1H, dd, J=9.8 Hz, 1.8 Hz), 7.08 (1H, dd, J=7.9 Hz, 2.4 Hz), 7.13 (1H, t, J=7.9 Hz), 7.38-7.50 (3H, m), 7.55 (1H, s).

Example 13

Ethyl(S)-2-allyl-2-t-butoxycarbonylamino-5-[2-chloro-4-(3-trifluoromethylphenylthio)phenyl]pentanoate

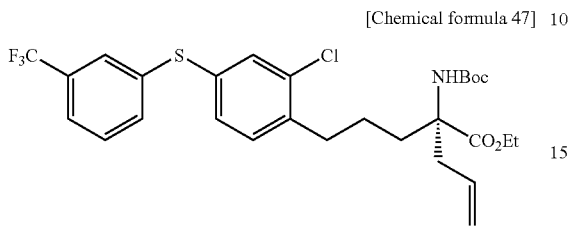

[Chemical formula 47]

The compound of Example 10 was reacted in the same manner as in Example 11 to obtain the target product as a colorless oil.

$^1$H-NMR (CDCl$_3$, 400 MHz) δ 1.24 (3H, t, J=7.3 Hz), 1.29-1.39 (1H, m), 1.43 (9H, s), 1.60-1.70 (1H, m), 1.78-1.86 (1H, m), 2.32-2.50 (2H, m), 2.66-2.73 (2H, m), 2.99-3.10 (1H, m), 4.19 (2H, q), 5.03 (1H, d, J=3.1 Hz), 5.09 (1H, s), 5.49 (1H, br s), 5.54-5.68 (1H, m), 7.16 (1H, d, J=7.9 Hz), 7.19 (1H, dd, J=7.9, 1.8 Hz), 7.35 (1H, d, J=1.8 Hz), 7.39-7.44 (2H, m), 7.45-7.50 (1H, m), 7.54 (1H, br s).

Example 14

Ethyl(R)-2-t-butoxycarbonylamino-5-[2-chloro-4-(3-trifluoromethylphenylthio)phenyl]-2-propylpentanoate

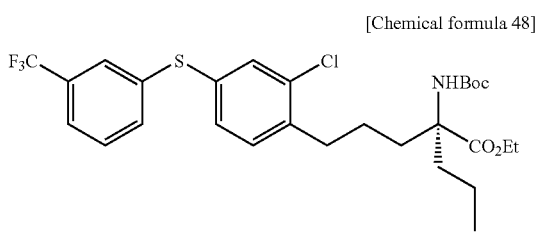

[Chemical formula 48]

To a solution of the compound of Example 13 (400 mg) in ethyl acetate (20 mL) was added palladium, on activated carbon/ethylene diamine complex (100 mg), and the resultant solution was stirred at room temperature for 24 hours under hydrogen atmosphere. The reaction solution was filtered through Celite, and the solvent was evaporated. The resultant residue was purified by silica gel column chromatography (hexane:ethyl acetate=30:1) to obtain the target product (293 mg) as a colorless oil.

$^1$H-NMR (CDCl$_3$, 400 MHz): δ 0.91 (3H, t, J=7.3 Hz), 1.42 (9H, s), 1.15-1.77 (8H, m), 2.72 (2H, t, J=7.3 Hz), 3.63 (1H, d, J=12 Hz), 3.67 (1H, d, J=12 Hz), 4.52 (1H, br s), 7.19-7.22 (2H, m), 7.39 (1H, s), 7.40-7.50 (3H, m), 7.54 (1H, br s).

FABMS (+): 532 [M+H]$^+$.

Example 15

(R)-2-t-butoxycarbonylamino-5-[2-chloro-4-(3-trifluoromethylphenoxy)phenyl]-2-methylpentan-1-ol

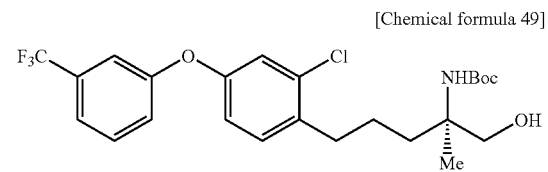

[Chemical formula 49]

To a solution of the compound of Example 11 (1.00 g) in THF (14 mL) was added under ice cooling lithium borohydride (229 mg), and then ethanol (1.4 mL) was added dropwise. The resultant solution was then stirred for 1 hour under ice cooling. To the reaction solution was added 10% aqueous citric acid, extracted with ethyl acetate, washed with water and saturated brine in that order, and then dried over anhydrous sodium sulfate. The solvent was evaporated, and the resultant residue was purified by silica gel column chromatography (hexane:ethyl acetate=4:1) to obtain the target product (910 mg) as a colorless oil.

$^1$H-NMR (CDCl$_3$, 400 MHz): δ 1.16 (3H, s), 1.43 (9H, s), 1.53-1.74 (3H, m), 1.81-1.93 (1H, m), 2.73 (2H, t, J=7.3 Hz), 3.61 (1H, d, J=12 Hz), 3.65 (1H, d, J=12 Hz), 4.58 (1H, br s), 4.58 (1H, br s), 6.86 (1H, dd, J=7.9, 2.4 Hz), 7.03 (1H, d, J=2.4 Hz), 7.16 (1H, dd, J=7.9 Hz, 2.4 Hz), 7.21 (1H, d, J=7.9 Hz), 7.24 (1H, br s), 7.37 (1H, d, J=7.9 Hz), 7.45 (1H, t, J=7.9 Hz).

Example 16

(R)-2-t-butoxycarbonylamino-5-[2-chloro-4-(3-trifluoromethylphenylthio)phenyl]-2-methylpentan-1-ol

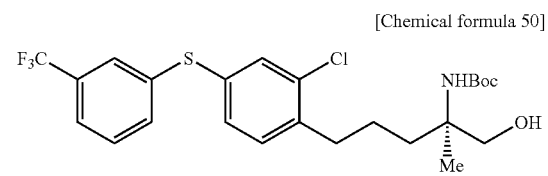

[Chemical formula 50]

The compound of Example 2 was reacted in the same manner as in Example 11 to obtain an ester, which was then reacted in the same manner as in Example 15 to obtain the target product as a colorless oil.

$^1$H-NMR (CDCl$_3$, 400 MHz): δ 1.14 (3H, s), 1.42 (9H, s), 1.48-1.76 (4H, m), 1.81-1.90 (1H, m), 2.74 (2H, t, J=6.7 Hz), 3.61 (1H, d, J=12 Hz), 3.65 (1H, d, J=12 Hz), 4.56 (1H, br s), 4.58 (1H, br s), 7.20 (2H, d, J=1.2 Hz), 7.37-7.50 (4H, m), 7.54 (1H, br s). Optical Rotation: [α]$_D^{27}$+14.31 (c 0.63, CHCl$_3$).

Example 17

(R)-2-t-butoxycarbonylamino-4-[2-chloro-4-(3-trifluoromethylphenoxy)phenyl]-2-methylbutan-1-ol

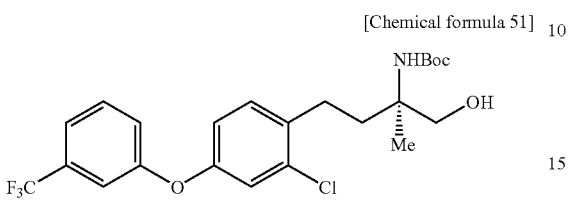

[Chemical formula 51]

The compound of Example 3 was reacted in the same manner as in Example 11 to obtain an ester, which was then reacted in the same manner as in Example 15 to obtain the target product as a colorless oil.

$^1$H-NMR (CDCl$_3$, 400 MHz): δ 1.26 (3H, s), 1.45 (9H, s), 1.80-1.88 (1H, m), 2.05-2.12 (1H, m), 2.66-2.80 (2H, m), 3.68 (1H, d, J=11.6 Hz), 3.73 (1H, d, J=11.6 Hz), 4.70 (1H, br s), 6.86 (1H, dd, J=8.5, 2.5 Hz), 7.03 (1H, d, J=2.5 Hz), 7.13-7.16 (1H, m), 7.22-7.24 (2H, m), 7.37 (1H, d, J=7.9 Hz), 7.45 (1H, t, J=7.9 Hz).

FABMS (+): 474 [M+H]$^+$.

Example 18

(R)-2-t-butoxycarbonylamino-4-[2-chloro-4-(3-trifluoromethylphenylthio)phenyl]-2-methylbutan-1-ol

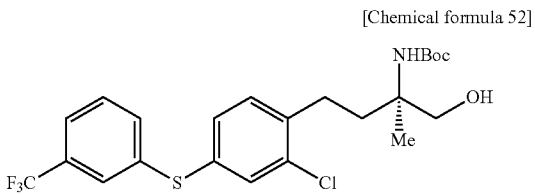 [SMILES: CC(C)(C)OC(=O)N[C@@](C)(CO)CCc1ccc(Sc2cccc(C(F)(F)F)c2)cc1Cl]

[Chemical formula 52]

The compound of Example 4 was reacted in the same manner as in Example 11 to obtain an ester, which was then reacted in the same manner as in Example 15 to obtain the target product as a colorless oil.

$^1$H-NMR (CDCl$_3$, 400 MHz): δ 1.25 (3H, s), 1.44 (9H, s), 1.79-1.89 (1H, m), 2.05-2.13 (1H, m), 2.66-2.83 (2H, m), 3.68 (1H, d, J=12 Hz), 3.71 (1H, d, J=12 Hz), 4.69 (1H, br s), 7.20-7.23 (2H, m), 7.37-7.42 (3H, m), 7.45-7.50 (2H, m), 7.55 (1H, br s).

Example 19

(R)-2-t-butoxycarbonylamino-4-[2-chloro-4-(3-ethylphenylthio)phenyl]-2-methylbutan-1-ol

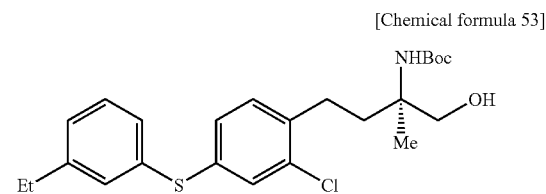 [SMILES: CCc1cccc(Sc2ccc(CC[C@](C)(CO)NC(=O)OC(C)(C)C)c(Cl)c2)c1]

[Chemical formula 53]

The compound of Example 5 was reacted in the same manner as in Example 11 to obtain an ester, which was then reacted in the same manner as in Example 15 to obtain the target product as a colorless oil.

$^1$H-NMR (CDCl$_3$, 400 MHz): δ 1.22 (3H, t, J=7.3 Hz), 1.24 (3H, s), 1.44 (9H, s), 1.77-1.85 (1H, m), 2.02-2.09 (1H, m), 2.62 (2H, q, J=7.3 Hz), 2.63-2.78 (2H, m), 3.64-3.73 (2H, m), 4.08 (1H, br), 4.68 (1H, br s), 7.10-7.17 (4H, m), 7.22-7.28 (3H, m).

ESIMS (+): 450 [M+H]$^+$.

Example 20

(R)-2-t-butoxycarbonylamino-5-[2-chloro-4-(3-methylphenoxy)phenyl]-2-methylpentan-1-ol

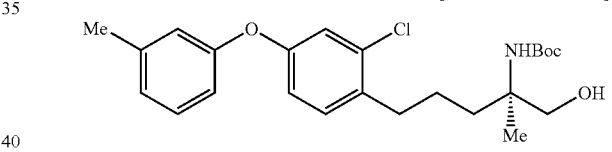

[Chemical formula 54]

The compound of Example 6 was reacted in the same manner as in Example 11 to obtain an ester, which was then reacted in the same manner as in Example 15 to obtain the target product as a colorless oil.

$^1$H-NMR (CDCl$_3$, 400 MHz): δ 1.15 (3H, s), 1.43 (9H, s), 1.61-1.67 (3H, m), 1.83-1.87 (1H, m), 2.34 (3H, s), 2.70 (2H, t, J=7.0 Hz), 3.62-3.65 (2H, m), 4.57 (1H, s), 6.81-6.84 (3H, m), 6.94 (1H, d, J=7.3 Hz), 6.98 (1H, d, J=3.1 Hz), 7.15 (1H, d, J=7.9 Hz), 7.22 (1H, t, J=7.9 Hz).

ESIMS (+): 434 [M+H]$^+$.

Example 21

(R)-2-t-butoxycarbonylamino-5-[2-chloro-4-(3-ethylphenylthio)phenyl]-2-methylpentan-1-ol

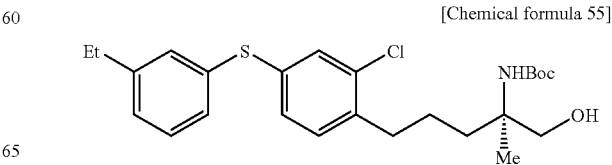

[Chemical formula 55]

The compound of Example 7 was reacted in the same manner as in Example 11 to obtain an ester, which was then reacted in the same manner as in Example 15 to obtain the target product as a colorless oil.

$^1$H-NMR (CDCl$_3$, 400 MHz): δ 1.14 (3H, s), 1.22 (3H, t, J=7.3 Hz), 1.43 (9H, s), 1.54-1.70 (3H, m), 1.79-1.89 (1H, m), 2.62 (2H, q, J=7.3 Hz), 2.70 (2H, t, J=7.0 Hz), 3.57-3.66 (2H, m), 4.05 (1H, br), 4.55 (1H, br s), 7.10-7.17 (4H, m), 7.17-7.28 (3H, m).

ESIMS (+): 464 [M+H]$^+$.

Example 22

(R)-2-t-butoxycarbonylamino-5-[2-chloro-4-(3-propylphenoxy)phenyl]-2-methylpentan-1-ol

[Chemical formula 56]

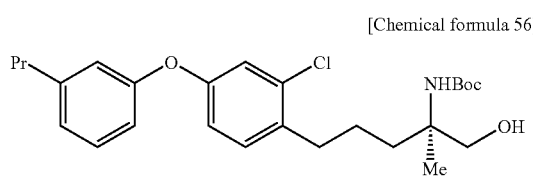 [SMILES: CC(C)(C)OC(=O)N[C@@](C)(CO)CCCc1ccc(Sc2cccc(Cl)c2)cc1Cl]

The compound of Reference Example 15 and (5S)-3,6-diethoxy-5-isopropyl-2-methyl-2,5-dihydropyrazine were reacted with in the same manner as in Example 1. The resultant compound was reacted in the same manner as in Example 11 to obtain an ester, which was then reacted in the same manner as in Example 15 to obtain the target product as a colorless oil.

$^1$H-NMR (CDCl$_3$, 400 MHz): δ 0.94 (3H, t, J=7.3 Hz), 1.15 (3H, s), 1.24-1.28 (2H, m), 1.43 (9H, s), 1.60-1.69 (3H, m), 1.80-1.90 (1H, m), 2.57 (2H, t, J=7.6 Hz), 2.70 (2H, t, J=7.6 Hz), 3.58-3.67 (2H, m), 4.11 (1H, br s), 4.58 (1H, br s), 6.79-6.85 (3H, m), 6.95 (1H, d, J=7.9 Hz), 6.99 (1H, d, J=2.8 Hz), 7.15 (1H, d, J=8.3 Hz), 7.24 (1H, t, J=7.9 Hz).

Example 23

(R)-2-t-butoxycarbonylamino-5-[2-chloro-4-(3-chlorophenylthio)phenyl]-2-methylpentan-1-ol

[Chemical formula 57]

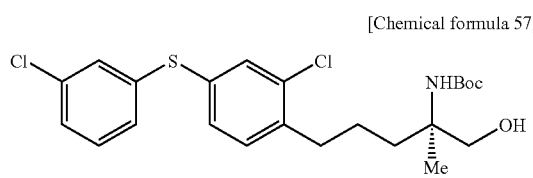

The compound of Example 8 was reacted in the same manner as in Example 11 to obtain an ester, which was then reacted in the same manner as in Example 15 to obtain the target product as a colorless oil.

$^1$H-NMR (CDCl$_3$, 400 MHz): δ 1.14 (3H, s), 1.43 (9H, s), 1.58-1.74 (3H, m), 1.79-1.92 (1H, m), 2.73 (2H, t, J=6.7 Hz), 3.61 (1H, d, J=12 Hz), 3.64 (1H, d, J=12 Hz), 4.08 (1H, br s), 4.57 (1H, br s), 7.17-7.27 (6H, m), 7.37 (1H, s).

ESIMS (+): 470 [M+H]

Example 24

(R)-2-t-butoxycarbonylamino-5-[2-fluoro-4-(3-trifluoromethylphenylthio)phenyl]-2-methylpentan-1-ol

[Chemical formula 58]

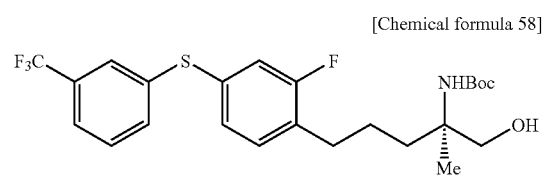

The compound of Example 12 was reacted in the same manner as in Example 15 to obtain the target product as a colorless oil.

$^1$H-NMR (CDCl$_3$, 400 MHz): δ 1.14 (3H, s), 1.42 (9H, s), 1.55-1.74 (3H, m), 1.75-1.85 (1H, m), 2.65 (2H, t, J=6.7 Hz), 3.58-3.64 (2H, m), 4.03 (1H, br s), 4.55 (1H, br s), 7.04 (1H, dd, J=9.8 Hz, 1.8 Hz), 7.10 (1H, dd, J=7.9 Hz, 1.8 Hz), 7.17 (1H, t, J=7.9 Hz), 7.38-7.50 (3H, m), 7.54 (1H, br s).

Example 25

(R)-2-t-butoxycarbonylamino-5-[2-chloro-4-(3-trifluoromethylphenylthio)phenyl]-2-propylpentan-1-ol

[Chemical formula 59]

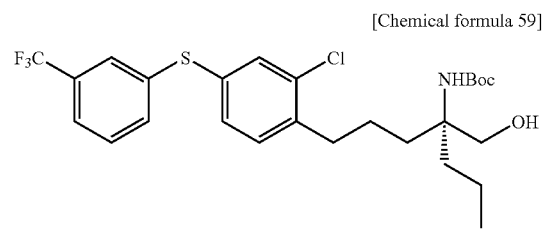 [SMILES: CCC[C@](CO)(CCCc1ccc(Sc2cccc(C(F)(F)F)c2)cc1Cl)NC(=O)OC(C)(C)C]

The compound of Example 14 was reacted in the same manner as in Example 15 to obtain the target product as a colorless oil.

$^1$H-NMR (CDCl$_3$, 400 MHz): δ 0.92 (3H, t, J=7.3 Hz), 1.42 (9H, s), 1.14-1.80 (8H, m), 2.72 (2H, t, J=7.3 Hz), 3.62 (1H, d, J=12 Hz), 3.66 (1H, d, J=12 Hz), 4.54 (1H, br s), 7.16-7.22 (2H, m), 7.39 (1H, s), 7.40-7.48 (3H, m), 7.55 (1H, br s).

FABMS (+): 532 [M+H]$^+$.

Example 26

(R)-2-amino-5-[2-chloro-4-(3-trifluoromethylphenoxy)phenyl]-2-methylpentan-1-ol hydrochloride

[Chemical formula 60]

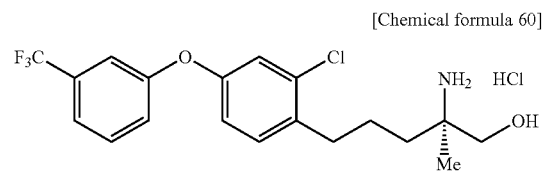 [SMILES: C[C@](N)(CO)CCCc1ccc(Oc2cccc(C(F)(F)F)c2)cc1Cl ; Cl]

To the compound of Example 15 (6.50 g) was added a 10 w/w % hydrogen chloride solution in methanol (methanol containing hydrogen chloride, 67 mL), and the resultant mixture was stirred for 1 hour at room temperature, and then left overnight at room temperature. The solvent was then evaporated to obtain the target product (5.15 g) as a colorless amorphous.

$^1$H-NMR (DMSO-d$_6$, 400 MHz): δ 1.07 (3H, s), 1.46-1.64 (4H, m), 2.62-2.72 (2H, m), 3.31-3.36 (2H, m), 7.03 (1H, dd, J=7.9, 2.4 Hz), 7.20 (1H, d, J=2.4 Hz), 7.30 (1H, d, J=7.9 Hz), 7.34 (1H, s), 7.39 (1H, d, J=7.9 Hz), 7.52 (1H, d, J=7.9 Hz), 7.63 (1H, t, J=7.9 Hz).

HREIMS (+): 388.1281 (Calcd. for C$_{19}$H$_{21}$NClF$_3$O$_2$: 388.1291).

Optical Rotation: $[\alpha]_D^{23}$ −2.74 (c 0.63, CHCl$_3$).

Example 27

(R)-2-amino-5-[2-chloro-4-(3-trifluoromethylphenylthio)phenyl]-2-methylpentan-1-ol hydrochloride

[Chemical formula 61]

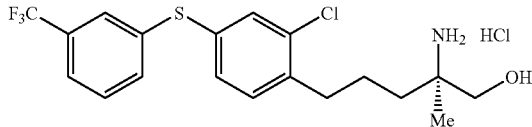

The compound of Example 16 was reacted in the same manner as in Example 26 to obtain the target product as a white powder.

$^1$H-NMR (DMSO-d$_6$, 400 MHz): δ 1.09 (3H, s), 1.49-1.63 (4H, m), 2.65-2.71 (2H, br s), 3.34 (1H, d, J=12 Hz), 3.38 (1H, d, J=12 Hz), 7.34 (1H, dd, J=7.9 Hz, 2.4 Hz), 7.41 (1H, d, J=7.9 Hz), 7.49 (1H, d, J=2.4 Hz), 7.55 (1H, d, J=7.9 Hz), 7.61 (1H, d, J=2.4 Hz), 7.67 (1H, d, J=7.9 Hz), 7.53-7.74 (3H, br s).

ESIMS (+): 404 [M+H]$^+$.

Elemental Analysis Measured: C, 51.65%; H, 4.86%; N, 2.86%. Calcd. for C$_{19}$H$_2$ClF$_3$NOS.HCl: C, 51.82%; H, 5.04%; N, 3.18%.

Optical Rotation: $[\alpha]_D^{23}$ −3.45 (c 1.00, CHCl$_3$).

Example 28

(R)-2-amino-4-[2-chloro-4-(3-trifluoromethylphenoxy)phenyl]-2-methylbutan-1-ol hydrochloride

[Chemical formula 62]

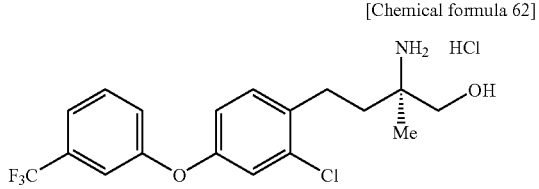

The compound of Example 17 was reacted in the same manner as in Example 26 to obtain the target product as a white powder.

$^1$H-NMR (DMSO-d$_6$, 400 MHz): δ 1.24 (3H, s), 1.70-1.80 (2H, m), 2.71 (2H, t, J=8.6 Hz), 3.44 (1H, dd, J=11 Hz, 4.9 Hz), 3.50 (1H, dd, J=11 Hz, 4.9 Hz), 5.54 (1H, t, J=4.9 Hz), 7.04 (1H, dd, J=8.6, 2.4 Hz), 7.21 (1H, d, J=2.4 Hz), 7.31 (1H, dd, J=8.6, 2.4 Hz), 7.35 (1H, br s), 7.41 (1H, d, J=8.6 Hz), 7.52 (1H, d, J=7.9 Hz), 7.63 (1H, t, J=7.9 Hz), 7.95 (3H, br s).

FABMS (+): 374 [M+H]$^+$.

Elemental Analysis Measured: C, 52.38%; H, 4.80%; N, 3.42%. Calcd. for C$_{18}$H$_{19}$ClF$_3$NO$_2$.HCl: C, 52.70%; H, 4.91%; N, 3.41%.

Example 29

(R)-2-amino-4-[2-chloro-4-(3-trifluoromethylphenylthio)phenyl]-2-methylbutan-1-ol hydrochloride

[Chemical formula 63]

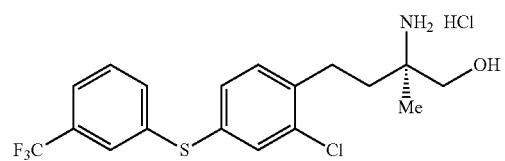

The compound of Example 18 was reacted in the same manner as in Example 26 to obtain the target product as a white powder.

$^1$H-NMR (DMSO-d$_6$, 400 MHz): δ 1.22 (3H, s), 1.66-1.83 (2H, m), 2.72 (2H, t, J=8.6 Hz), 3.42 (1H, dd, J=11.0, 7.9 Hz), 3.49 (1H, dd, J=11.0, 7.9 Hz), 5.54 (1H, t, J=4.9 Hz), 7.36 (1H, dd, J=7.9, 1.8 Hz), 7.42 (1H, d, J=7.9 Hz), 7.50 (1H, d, J=1.8 Hz), 7.53-7.64 (3H, m), 7.67 (1H, d, J=7.9 Hz), 7.82 (3H, br s).

FABMS (+): 390 [M+H]

Elemental Analysis: Measured: C, 50.47%; H, 4.65%; N, 3.36%. Calcd. for C$_{18}$H$_{19}$ClF$_3$NOS.HCl: C, 50.71%; H, 4.73%; N, 3.29%.

Optical Rotation: $[\alpha]_D^{27}$ +5.78 (c 0.33, CHCl$_3$).

Example 30

(R)-2-amino-4-[2-chloro-4-(3-ethylphenylthio)phenyl]-2-methylbutan-1-ol hydrochloride

[Chemical formula 64]

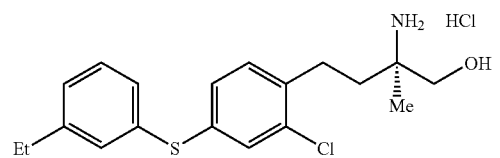

The compound of Example 19 was reacted in the same manner as in Example 26 to obtain the target product as a white powder.

$^1$H-NMR (DMSO-d$_6$, 400 MHz): δ 1.14 (3H, t, J=7.3 Hz), 1.22 (3H, s), 1.67-1.81 (2H, m), 2.59 (2H, q, J=7.3 Hz), 2.69 (2H, t, J=8.6 Hz), 3.42 (1H, dd, J=11.6, 5.5 Hz), 3.48 (1H, dd, J=11.6, 5.5 Hz), 5.52 (1H, t, J=4.9 Hz), 7.16-7.22 (2H, m), 7.26-7.27 (2H, m), 7.30-7.35 (2H, m), 7.93 (3H, br s).

ESIMS (+): 350 [M+H]$^+$.

Elemental Analysis Measured: C, 58.90%; H, 6.42%; N, 3.59%. Calcd. for C$_{19}$H$_{24}$ClNOS.HCl: C, 59.06%; H, 6.52%; N, 3.63%.

Example 31

(R)-2-amino-5-[2-chloro-4-(3-methylphenoxy)phenyl]-2-methylpentan-1-ol hydrochloride

[Chemical formula 65]

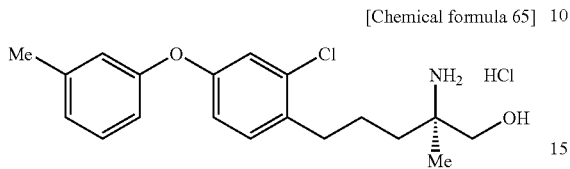

The compound of Example 20 was reacted in the same manner as in Example 26 to obtain the target product as a colorless amorphous.

$^1$H-NMR (DMSO-$d_6$, 400 MHz): δ 1.11 (3H, s), 1.57 (4H, brs), 2.29 (3H, s), 2.64 (2H, brs), 3.35-3.39 (2H, m), 5.45 (1H, t, J=4.9 Hz), 6.81 (1H, dd, J=8.6, 2.4 Hz), 6.85 (1H, s), 6.92 (1H, dd, J=8.6, 2.4 Hz), 6.99 (1H, d, J=8.6 Hz), 7.03 (1H, d, J=2.4 Hz), 7.28 (1H, t, J=8.6 Hz), 7.34 (1H, d, J=8.6 Hz), 7.77 (3H, brs).

HRESIMS (+): 334.15655 (Calcd. for $C_{19}H_{25}ClNO_2$: 334.15738).

Optical Rotation: $[\alpha]_D^{263}$ -5.75 (c 0.60, $CHCl_3$).

Example 32

(R)-2-amino-5-[2-chloro-4-(3-ethylphenylthio)phenyl]-2-methylpentan-1-ol hydrochloride

[Chemical formula 66]

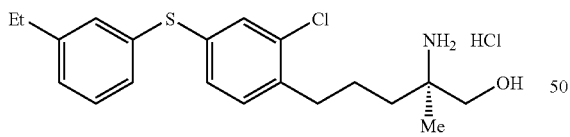

The compound of Example 21 was reacted in the same manner as in Example 26 to obtain the target product as a colorless oil.

$^1$H-NMR (DMSO-$d_6$, 400 MHz): δ 1.10 (3H, s), 1.15 (3H, t, J=7.3 Hz), 1.52-1.58 (4H, m), 2.59 (2H, q, J=7.3 Hz), 2.62-2.66 (2H, m), 3.32-3.39 (2H, m), 5.43 br), 7.15-7.22 (3H, m), 7.26 (2H, d, J=1.8 Hz), 7.32 (2H, dd, J=7.3, 1.8 Hz), 7.81 (3H, br s).

HRESIMS (+): 364.15051 (Calcd. for $C_{20}H_{27}ClNOS$: 364.15019).

Example 33

(R)-2-amino-5-[2-chloro-4-(3-propylphenoxy)phenyl]-2-methylpentan-1-ol hydrochloride

[Chemical formula 67]

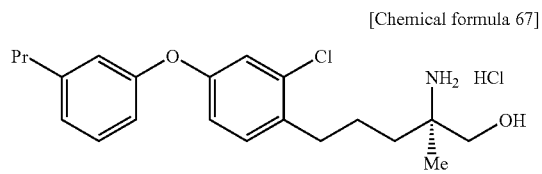

The compound of Example 22 was reacted in the same manner as in Example 26 to obtain the target product as a colorless amorphous.

$^1$H-NMR (DMSO-$d_6$, 400 MHz): δ 0.86 (3H, t, J=7.3 Hz), 1.11 (3H, s), 1.51-1.61 (6H, m), 2.53 (2H, t, J=7.3 Hz), 2.63 (2H, t, J=6.7 Hz), 3.34-3.42 (2H, m), 5.45 (1H, t, J=4.9 Hz), 6.81 (1H, ddd, J=7.9, 1.8, 0.9 Hz), 6.87 (1H, t, J=1.8 Hz), 6.91 (1H, dd, J=8.6, 2.4 Hz), 7.00 (1H, d, J=7.9 Hz), 7.02 (1H, d, J=2.4 Hz), 7.30 (1H, t, J=7.9 Hz), 7.34 (1H, d, J=8.6 Hz), 7.85 (3H, br s).

ESIMS (+): 362 [M+H]$^+$.

HRESIMS (+): 362.19198 (Calcd. for $C_{21}H_{29}ClNO_2$: 362.18868).

Optical Rotation: $[\alpha]_D^{25.1}$ -4.46 (c 1.27, $CHCl_3$).

Example 34

(R)-2-amino-5-[2-chloro-4-(3-chlorophenylthio)phenyl]-2-methylpentan-1-ol hydrochloride

[Chemical formula 68]

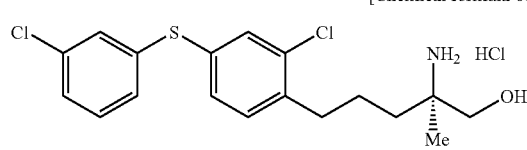

The compound of Example 23 was reacted in the same manner as in Example 26 to obtain the target product as a colorless amorphous.

$^1$H-NMR (DMSO-$d_6$, 400 MHz): δ 1.10 (3H, s), 1.49-1.64 (4H, m), 2.68 (2H, br s), 3.33 (1H, dd, J=12, 4.9 Hz), 3.38 (1H, dd, J=12, 4.9 Hz), 5.45 (1H, t, J=4.9 Hz), 7.26 (1H, dt, J=7.3, 1.8 Hz), 7.30-7.43 (5H, m), 7.45 (1H, d, J=1.8 Hz), 7.77 (3H, br s).

HREIMS (+): 370.0 799 (Calcd. for $C_{18}H_{21}Cl_2NOS$: 370.0799).

Optical Rotation: $[\alpha]_D^{27}$ -3.81 (c 0.50, $CHCl_3$).

Example 35

(R)-2-amino-5-[2-fluoro-4-(3-trifluoromethylphenylthio)phenyl]-2-methylpentan-1-ol hydrochloride

[Chemical formula 69]

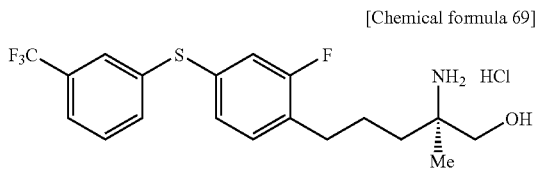 [SMILES: Cc1cccc(Oc2ccc(CCC[C@@](C)(N)CO)c(Cl)c2)c1 ; Cl]

The compound of Example 24 was reacted in the same manner as in Example 26 to obtain the target product as a colorless amorphous.

$^1$H-NMR (DMSO-$d_6$, 400 MHz): δ 1.09 (3H, s), 1.48-1.61 (4H, m), 2.57-2.64 (2H, br s), 3.32 (1H, dd, J=11, 4.9 Hz), 3.37 (1H, dd, J=11, 4.9 Hz), 5.44 (1H, t, J=4.9 Hz), 7.20 (1H, dd, J=7.9, 1.8 Hz), 7.26 (1H, dd, J=9.8, 1.8 Hz), 7.37 (1H, t, J=7.9 Hz), 7.54-7.68 (4H, m), 7.74 (3H, br s).

HRESIMS (+): 388.1345 (Calcd. for $C_{19}H_{22}F_4NOS$: 388.1358).

Optical Rotation: $[α]_D^{24}$ −3.23 (c 0.69, $CHCl_3$).

Example 36

(R)-2-amino-5-[2-chloro-4-(3-trifluoromethylphenylthio)phenyl]-2-propylpentan-1-ol hydrochloride

[Chemical formula 70]

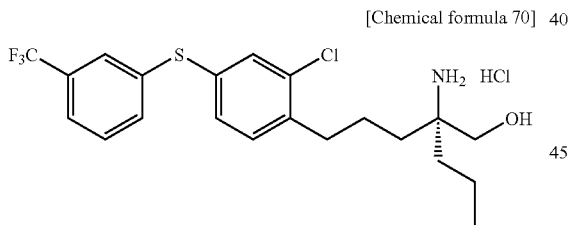

The compound of Example 25 was reacted in the same manner as in Example 26 to obtain the target product as a white powder.

$^1$H-NMR (DMSO-$d_6$, 400 MHz): δ 0.84 (3H, t, J=7.3 Hz), 1.20 (2H, q, J=7.3 Hz), 1.36-1.63 (6H, m), 2.68 (2H, t, J=7.3 Hz), 3.36 (2H, d, J=4.9 Hz), 5.40 (1H, d, J=4.9 Hz), 7.35 (1H, dd, J=7.9 Hz, 1.8 Hz), 7.42 (1H, d, J=7.9 Hz), 7.50 (1H, d, J=1.8 Hz), 7.55 (1H, d, J=7.9 Hz), 7.58-7.63 (2H, m), 7.67 (1H, d, J=7.9 Hz), 7.69 (3H, br s).

FABMS (+): 432 [M+H]$^+$.

Elemental Analysis Measured: C, 53.46%; H, 5.62%; N, 2.98%. Calcd. for $C_{21}H_{25}ClF_3NOS·HCl$: C, 53.85%; H, 5.59%; N, 2.99%.

Optical Rotation: $[α]_D^{23}$ +3.85 (c 0.63, $CHCl_3$).

Example 37

(R)-2-amino-5-[2-chloro-4-(3-trifluoromethylphenylthio)phenyl]-2-methylpentan-1-ol

[Chemical formula 71]

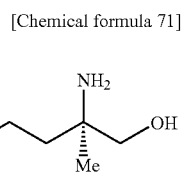

To a solution of the compound of Example 27 (9.3 g) in ethyl acetate (450 mL) was added saturated aqueous sodium hydrogen carbonate solution (450 mL), and the resultant solution was stirred at room temperature for 10 minutes. The organic layer was washed with water and saturated brine in that order, and then dried over anhydrous sodium sulfate. The solvent was evaporated, and the resultant residue was purified by NH-silica gel column chromatography (ethyl acetate:methanol=4:1) to obtain the target product (8.9 g) as a white powder.

$^1$H-NMR (DMSO-$d_6$, 400 MHz): δ 0.85 (3H, s), 1.21 (2H, br s), 1.28 (2H, t, J=8.6 Hz), 1.46-1.67 (2H, m), 2.65 (2H, t, J=8.6 Hz), 3.06 (2H, br s), 4.49 (1H, br s), 7.32 (1H, dd, J=7.9, 1.8 Hz), 7.40 (1H, d, J=9.8 Hz), 7.47 (1H, d, J=1.8 Hz), 7.54 (1H, dd, J=6.7, 1.8 Hz), 7.56-7.62 (2H, m), 7.65 (1H, dd, J=6.7, 1.8 Hz).

ESIMS (+): 404 [M+H]$^+$.

Elemental Analysis Measured: C, 56.26%; H, 5.14%; N, 3.40%. Calcd. for $C_{19}H_{21}ClF_3NOS$: C, 56.50%; H, 5.24%; N, 3.47%.

Example 38

Diethyl 2-{3-[2-chloro-4-(3-trifluoromethylphenylthio)phenyl]propyl}-2-methylmalonate

[Chemical formula 72]

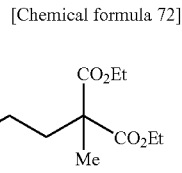

2-Chloro-1-(3-iodopropyl)-4-(3-trifluoromethylphenylthio)benzene and diethyl 2-methylmalonate were reacted according to the same procedures as in Example 152 of WO 04026817 to obtain the target product as a colorless oil.

$^1$H-NMR ($CDCl_3$, 400 MHz): δ 1.25 (6H, t, J=7.4 Hz), 1.40 (3H, s), 1.51-1.63 (2H, m), 1.90-1.97 (2H, m), 2.73 (2H, t, J=7.9 Hz), 4.17 (4H, q, J=7.4 Hz), 7.17-7.23 (2H, m), 7.38 (1H, d, J=2.2 Hz), 7.39-7.44 (2H, m), 7.45-7.50 (1H, m), 7.55 (1H, s).

EIMS (+): 502 [M]$^+$.

Example 39

(±)-5-[2-chloro-4-(3-trifluoromethylphenylthio)phenyl]-2-ethoxycarbonyl-2-methylpentanoic acid

[Chemical formula 73]

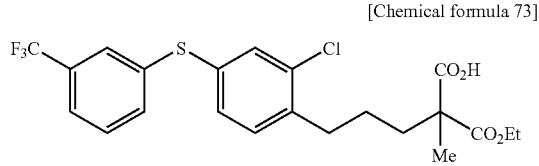 [SMILES: CCOC(=O)C(C)(CCCc1ccc(Sc2cccc(C(F)(F)F)c2)cc1Cl)C(=O)OCC]

To a solution of the compound of Example 38 (16.8 g) in ethanol (167 mL) was added potassium hydroxide (2.40 g), and the resultant solution was stirred at 50° C. for 24 hours. To the reaction solution was added water, neutralized with 2 mol/L aqueous hydrochloric acid, and extracted with ethyl acetate. The organic layer was washed with water and saturated brine in that order, and then dried over anhydrous sodium sulfate. The solvent was evaporated, and the resultant residue was purified by silica gel column chromatography (hexane:ethyl acetate=1:1) to obtain the target product (11.2 g) as a colorless oil.

$^1$H-NMR (CDCl$_3$, 400 MHz): δ 1.26 (3H, t, J=7.4 Hz), 1.47 (3H, s), 1.55-1.66 (2H, m), 1.87-2.06 (2H, m), 2.73 (2H, t, J=7.9 Hz), 4.22 (2H, q, J=7.4 Hz), 7.18 (1H, d, J=7.9 Hz), 7.20 (1H, dd, J=7.9, 1.8 Hz), 7.38 (1H, d, J=1.8 Hz), 7.39-7.44 (2H, m), 7.45-7.50 (1H, m), 7.54 (1H, s).

ESIMS (+): 475 [M+H]$^+$.

Example 40

Ethyl(±)-5-[2-chloro-4-(3-trifluoromethylphenylthio)phenyl]-2-methoxycarbonylamino-2-methylpentanoate

[Chemical formula 74]

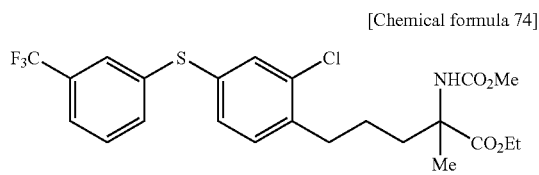

To a solution of the compound of Example 39 (15.8 g) in benzene (166 mL) was added diphenylphosphoryl azide (7.86 mL) and triethylamine (6.01 mL), and the resultant solution was heated to reflux for 1.5 hours. The temperature of the reaction solution was returned to room temperature, and methanol (20 mL) was added dropwise over 20 minutes. The resultant solution was heated to reflux for 30 minutes, and then further sodium methoxide (3.58 g) was added. The resultant solution was heated to reflux for 1.5 hours. To the reaction solution was added saturated aqueous ammonium chloride, and extracted with ethyl acetate. The organic layer was washed with water and saturated brine in that order, and then dried over anhydrous sodium sulfate. The solvent was evaporated, and the resultant residue was purified by silica gel column chromatography (hexane:ethyl acetate=5:1) to obtain the target product (15.6 g) as a colorless oil.

$^1$H-NMR (CDCl$_3$, 400 MHz): δ 1.25 (3H, t, J=7.3 Hz), 1.32-1.47 (1H, m), 1.52-1.67 (1H, m), 1.57 (3H, s), 1.80-1.90 (1H, m), 2.20-2.37 (1H, m), 2.62-2.76 (2H, m), 3.64 (3H, s), 4.15-4.25 (2H, m), 5.62 (1H, br s), 7.16 (1H, d, J=7.9 Hz), 7.20 (1H, dd, J=7.9, 1.8 Hz), 7.38 (1H, d, J=1.8 Hz), 7.40-7.44 (2H, m), 7.45-7.50 (1H, m), 7.55 (1H, s).

ESIMS (+): 504 [M+H]$^+$.

Example 41

(±)-5-[2-chloro-4-(3-trifluoromethylphenylthio)phenyl]-2-methoxycarbonyl amino-2-methylpentan-1-ol

[Chemical formula 75]

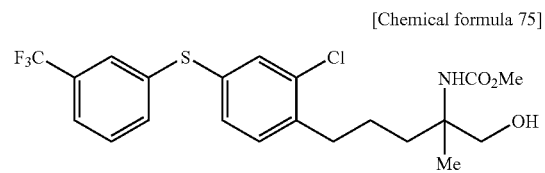

To a solution of the compound of Example 40 (15.6 g) in THF (249 mL) was added under ice cooling lithium borohydride (3.75 g), and then ethanol (16.6 mL) was added dropwise. The resultant solution was then stirred for 1 hour under ice cooling. To the reaction solution was added 10% aqueous citric acid, extracted with ethyl acetate, washed with water and saturated brine in that order, and then dried over anhydrous sodium sulfate. The solvent was evaporated, and the resultant residue was purified by silica gel column chromatography (hexane:ethyl acetate=1:1) to obtain the target product (12.9 g) as a colorless oil.

$^1$H-NMR (CDCl$_3$, 400 MHz): δ 1.18 (3H, s), 1.54-1.74 (3H, m), 1.78-1.89 (1H, m), 2.73 (2H, t, J=7.9 Hz), 3.63 (3H, s), 3.56-3.70 (2H, m), 4.23 (1H, br s), 7.17-7.22 (2H, m), 7.38-7.50 (4H, m), 7.54 (1H, s).

ESIMS (+): 462 [M+H]$^+$.

Example 42

(±)-2-t-butoxycarbonylamino-5-[2-chloro-4-(3-trifluoromethylphenylthio)phenyl]-2-methylpentan-1-ol

[Chemical formula 76]

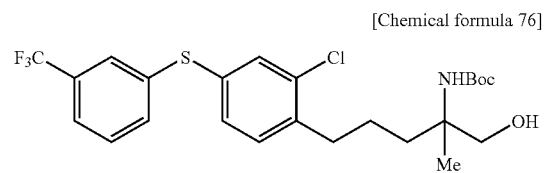 [SMILES: CC(CO)(CCCc1ccc(Sc2cccc(C(F)(F)F)c2)cc1Cl)NC(=O)OC(C)(C)C]

To a solution of the compound of Example 41 (12.9 g) in THF (60 mL) and methanol (120 mL) was added under ice cooling 5 mol/L aqueous potassium hydroxide solution (60 mL), and the resultant solution was heated to reflux for 86 hours. To the reaction solution was added water, extracted with ethyl acetate, washed with water and saturated brine in that order, and then dried over anhydrous sodium sulfate. The extract was concentrated, the residue was dissolved in 1,4-dioxane (279 mL), and the resultant solution was charged with di-tert-butoxydicarbonate (9.13 g). The solution was stirred at room temperature for 2 hours and then left to stand at room temperature overnight. The reaction solution was added water, extracted with ethyl acetate, washed with water and saturated brine in that order, and then dried over anhydrous sodium sulfate. The solvent was evaporated, and the resultant residue was purified by silica gel column chromatography (hexane:ethyl acetate=2:1) to obtain the target product (13.0 g) as a colorless oil.

$^1$H-NMR (CDCl$_3$, 400 MHz): δ 1.14 (3H, s), 1.42 (9H, s), 1.53-1.74 (3H, m), 1.79-1.92 (1H, m), 2.74 (2H, t, J=7.9 Hz), 3.58-3.69 (2H, m), 4.05 (1H, br s), 4.57 (1H, br s), 7.20-7.22 (2H, m), 7.38-7.50 (4H, m), 7.54 (1H, s).

ESIMS (+): 504 [M+H]$^+$.

Examples 43 and 44

(+)-2-t-butoxycarbonylamino-5-[2-chloro-4-(3-trifluoromethylphenylthio)phenyl]-2-methylpentan-1-ol and (−)-2-t-butoxycarbonylamino-5-[2-chloro-4-(3-trifluoromethylphenylthio)phenyl]-2-methylpentan-1-ol The compound of Example 42 was subjected to optical resolution using high performance liquid chromatography (CHIRALCEL OJ-H, hexane:isopropanol:diethylamine=98:2:0.1 (v/v), measurement wavelength: UV 278 nm, flow rate: 1.0 mL/min). From the pre-elution portion, an $[α]_D^{25}$+15.08 (c 0.63, CHCl$_3$) colorless oil was obtained (Example 43), and from the post-elution portion, an $[α]_D^{26}$−13.91 (c 0.63, CHCl$_3$) colorless oil was obtained (Example 44).

Example 45

(−)-2-Amino-5-[2-chloro-4-(3-trifluoromethylphenylthio)phenyl]-2-methylpentan-1-ol hydrochloride The compound of Example 43 was reacted in the same manner as in Example 26 to obtain the target product as a white powder.

ESIMS (+): 404 [M+H]$^+$.

Optical Rotation: $[α]_D^{25}$-4.48 (c 1.00, CHCl$_3$).

Test Example

Effect on SCID CD4$^+$ CD45RB$^{high}$ T Cell Transfer Colitis Model

SCID CD4$^+$ CD45RB$^{high}$ T cell transfer colitis model has been reported as a model resembling to Crohn's disease due to its histopathological characteristics and the produced cytokines (Powrie F et al, Immunity, 1, 553-562, 1994). In addition, this model has also been used for evaluation of a medicine which is used in the treatment of inflammatory bowel disease and its effectiveness has been reported (Liu Z et al., J. Autoimmunl., 29, 187-194, 2007).

C.B-17/Icr-scid/scid Jcl (SCID mice) (female, 8 weeks of age, mouse to be transferred) and BALB/c Cr Slc (BALB/c mice) (female, 8 weeks of age, mouse for transfer cell preparation) were obtained and used in the test. CD4$^+$ CD45RB$^{high}$ T cells (naive T cells) prepared from the spleen of BALB/c mice were transferred intraperitoneally into the SCID mice at a concentration of 3×10$^5$ cells/body, and then colitis was induced by breeding it for 4 weeks. Preparation of the CD4$^+$ CD45RB$^{high}$ T cells was carried out in accordance with the method of Uraushihara et al. (J. Immunol., 171, 708-716, 2003) and FACSAriaCell Sorter (Becton Dickinson Japan) was used as a cell separator.

The compound produced in Example 27 (compound 27) was dissolved in distilled water and orally administered at doses of 0.3 mg/kg, 1 mg/kg and 3 mg/kg, once a day for 4 weeks starting on the preceding day of cell transfer. Distilled water alone was administered to the vehicle group. Body weight was determined every day during the administration period. The change ratio (%) of the body weight on the determination day was calculated based on the body weight on the day of the start of administration. On the next day of final administration, blood was collected and the large intestine was extracted. The total number of leukocytes was measured using the collected blood. After fixing the extracted large intestine with formalin, tissue sections were prepared and hematoxylin-eosin staining was carried out. Evaluation was performed in accordance with the scoring system (Uraushihara K et al., J. Immunol., 171, 708-716, 2003). That is, the large intestine was roughly divided into 3 regions (proximal region, middle region and distal region), and scoring was carried out on the 3 layers, which are mucosa, submucosa and muscularis, of each region. By totaling the obtained scores of each region, the value having the highest total score among the three regions was used as the score of the individual. The change ratio of the body weight and the total number of leukocytes were shown by mean±standard error and the pathological score was shown by median.

As shown in Table 1, body weight loss and the total number of leukocytes were significantly suppressed by the administration of compound 27 in comparison with the vehicle group. In addition, suppressive effect was found regarding the pathological score. From these results, it was revealed that the compound 27 shows the suppressive effect on the SCID CD4$^+$ CD45RB$^{high}$ T cell transfer colitis model.

TABLE 1

| Test group | Change ratio of body weight (%) | | Total number of leukocytes (cells/μL) | Pathological score |
|---|---|---|---|---|
| | On the third week | On the fourth week | | |
| Vehicle group | −5.2 ± 1.9 | −7.6 ± 1.6 | 3211 ± 393 | 7 |
| Compound 27 (0.3 mg/kg) | 1.1 ± 1.4 ** | −1.0 ± 2.2 | 2733 ± 561 | 5 |
| Compound 27 (1 mg/kg) | 1.5 ± 0.8 ** | −1.4 ± 2.0 | 1980 ± 241 | 5 |
| Compound 27 (3 mg/kg) | 0.5 ± 1.2 * | −0.8 ± 2.0 * | 1720 ± 327 * | 3.5 |

The number of animals: 8 to 10

* <0.05 vs vehicle group (Dunnett's test)

** <0.01 vs vehicle group (Dunnett's test)

Formulation Example

| Composition | |
|---|---|
| Compound 27 | 0.1 mg |
| D-mannitol | 247.5 mg |
| Magnesium stearate | 2.5 mg |

A mixed powder was produced by mixing the compound 27 with D-mannitol and further mixing magnesium stearate therewith. A capsule preparation was produced by filling this mixed powder in a capsule.

INDUSTRIAL APPLICABILITY

It became possible to provide a pharmaceutical which is useful for the treatment or prevention of inflammatory bowel disease by the compound of the invention.

The invention claimed is:

1. A method of treating an inflammatory bowel disease, the method comprising administering to a patient in need thereof, an effective amount of a (R)-2-amino-5-[2-chloro-4-(3-trifluoromethylphenylthio)phenyl]-2-methylpentan-1-ol, or a pharmaceutically acceptable salt thereof.

2. A method of treating an inflammatory bowel disease, the method comprising administering to a patient in need thereof, an effective amount of a (−)-2-amino-5-[2-chloro-4-(3-trifluoromethylphenylthio)phenyl]-2-methylpentan-1-ol, or a pharmaceutically acceptable salt thereof,
wherein the (−)-2-amino-5-[2-chloro-4-(3-trifluoromethylphenylthio)phenyl]-2-methylpentan-1-ol, or a pharmaceutically acceptable salt thereof, is obtained by:
allowing a compound represented by formula (2) and a compound represented by formula (10) to react with each other in the presence of a base,

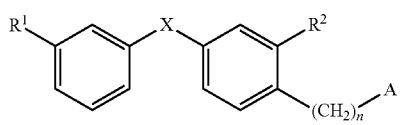

(2)

wherein $R^1$ represents a trifluoromethyl group, $R^2$ represents a chlorine atom, A represents a halogen atom, X represents a sulfur atom, and n denotes 3,

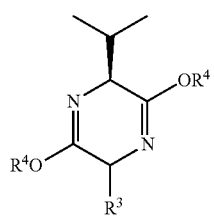

(10)

wherein $R^3$ represents a methyl group and $R^4$ represents an alkyl group having 2 carbon atoms,
subjecting a resultant product to acidolysis,
protecting a nitrogen atom with a t-butoxycarbonyl group,
reducing a resultant protected compound, and
deprotecting the nitrogen atom of a resultant reduced compound.

3. A method of treating an inflammatory bowel disease, the method comprising administering to a patient in need thereof, an effective amount of a (−)-2-amino-5-[2-chloro-4-(3-trifluoromethylphenylthio)phenyl]-2-methylpentan-1-ol or a pharmaceutically acceptable salt thereof.

4. A method of treating an inflammatory bowel disease, the method comprising administering to a patient in need thereof, an effective amount of a (R)-2-amino-5-[2-chloro-4-(3-trifluoromethylphenylthio)phenyl]-2-methylpentan-1-ol, or a pharmaceutically acceptable salt thereof,
wherein the (R)-2-amino-5-[2-chloro-4-(3-trifluoromethylphenylthio)phenyl]-2-methylpentan-1-ol, or a pharmaceutically acceptable salt thereof, is obtained by:
allowing a compound represented by formula (2) and a compound represented by formula (10) to react with each other in the presence of a base,

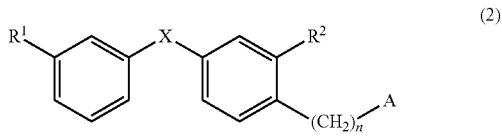

(2)

wherein $R^1$ represents a trifluoromethyl group, $R^2$ represents a chlorine atom, A represents a halogen atom, X represents a sulfur atom, and n denotes 3,

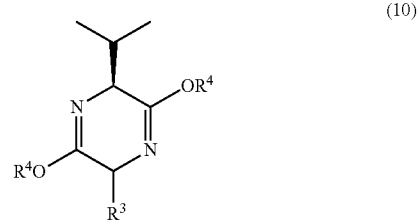

(10)

wherein $R^3$ represents a methyl group and $R^4$ represents an alkyl group having 2 carbon atoms,
subjecting a resultant product to acidolysis,
protecting a nitrogen atom with a t-butoxycarbonyl group,
reducing a resultant protected compound, and
deprotecting the nitrogen atom of a resultant reduced compound.

* * * * *